United States Patent [19]

Hashiguchi et al.

[11] Patent Number: 5,496,347
[45] Date of Patent: Mar. 5, 1996

[54] SURGICAL INSTRUMENT

[75] Inventors: Toshihiko Hashiguchi, Sagamihara; Toshiya Sugai; Katsumi Sasaki, both of Tokyo, all of Japan

[73] Assignee: Olympus Optical Co., Ltd., Tokyo, Japan

[21] Appl. No.: 218,976

[22] Filed: Mar. 28, 1994

[30] Foreign Application Priority Data

Mar. 30, 1993 [JP] Japan ................... 5-072552
Apr. 5, 1993 [JP] Japan ................... 5-078253
Apr. 12, 1993 [JP] Japan ................... 5-084881
Apr. 30, 1993 [JP] Japan ................... 5-104633
Apr. 30, 1993 [JP] Japan ................... 5-104634
Apr. 30, 1993 [JP] Japan ................... 5-104635

[51] Int. Cl.⁶ ........................ A61B 17/28; A61B 17/32
[52] U.S. Cl. ..................... 606/205; 606/174; 128/751
[58] Field of Search ............... 606/51, 52, 174, 606/167, 170, 205–210; 128/750–755

[56] References Cited

U.S. PATENT DOCUMENTS

| | | | |
|---|---|---|---|
| 4,712,545 | 12/1987 | Honkanen | 128/751 |
| 4,976,723 | 12/1990 | Schad | 128/751 |
| 5,052,402 | 10/1991 | Bencini et al. | 128/751 |
| 5,147,357 | 9/1992 | Rose et al. | 606/52 |
| 5,176,702 | 1/1993 | Bales et al. | 128/751 |
| 5,209,747 | 5/1993 | Knoepfler | 606/208 |
| 5,282,806 | 2/1994 | Haber et al. | 606/207 |

FOREIGN PATENT DOCUMENTS

| | | |
|---|---|---|
| 0503662A1 | 5/1992 | European Pat. Off. . |
| 0484671A2 | 5/1992 | European Pat. Off. . |
| 8809501 | 1/1989 | Germany . |
| 4-246344 | 9/1992 | Japan . |

Primary Examiner—Stephen C. Pellegrino
Assistant Examiner—William W. Lewis
Attorney, Agent, or Firm—Frishauf, Holtz, Goodman, Langer & Chick

[57] ABSTRACT

A surgical instrument for treatment in the body cavity, in which an open-close member for treatment is rockably mounted by of a pivot pin on the distal end portion of a sheath to be inserted into the body cavity, and is connected to the distal end of a rod passed through the sheath, by a cam mechanism including a cam groove and a cam pin in engagement therewith. As the rod is moved by an operating handle, the cam mechanism is activated to open and close the open-close member for treatment. The component members of the cam mechanism have external shapes such that those portions on the proximal end side of the position near the pivot pin do not project from the sheath in every operating state.

20 Claims, 18 Drawing Sheets

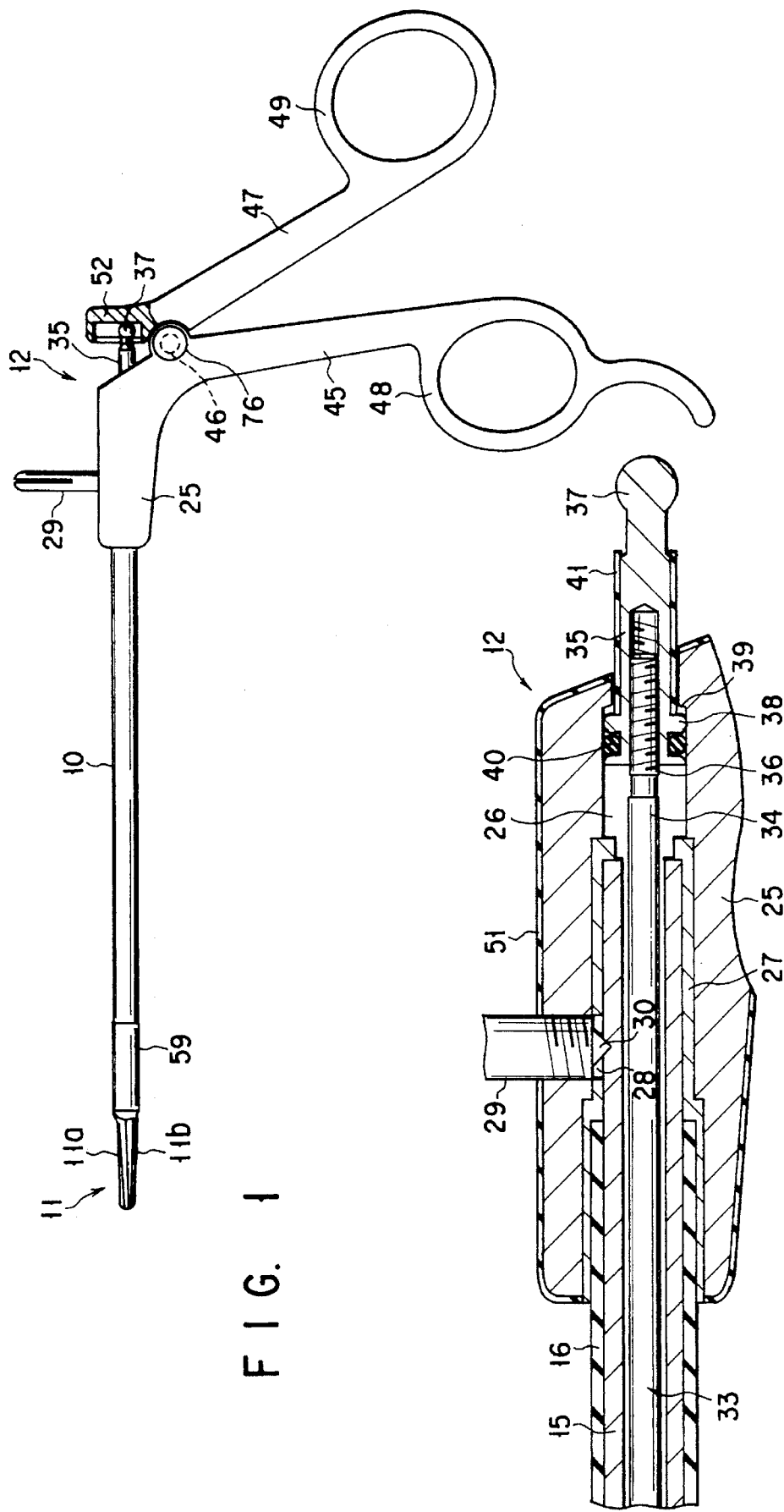

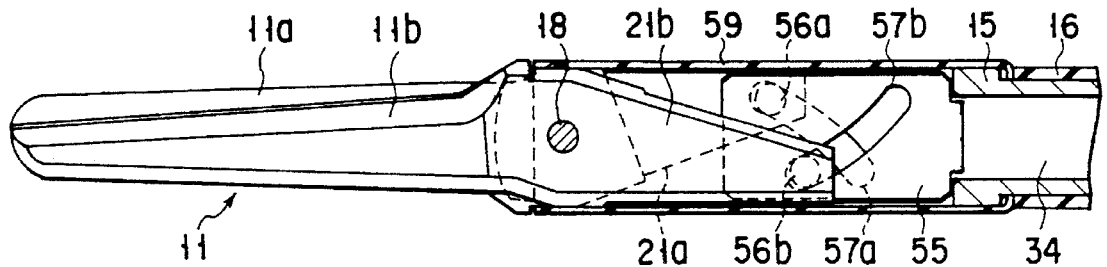
F I G. 7
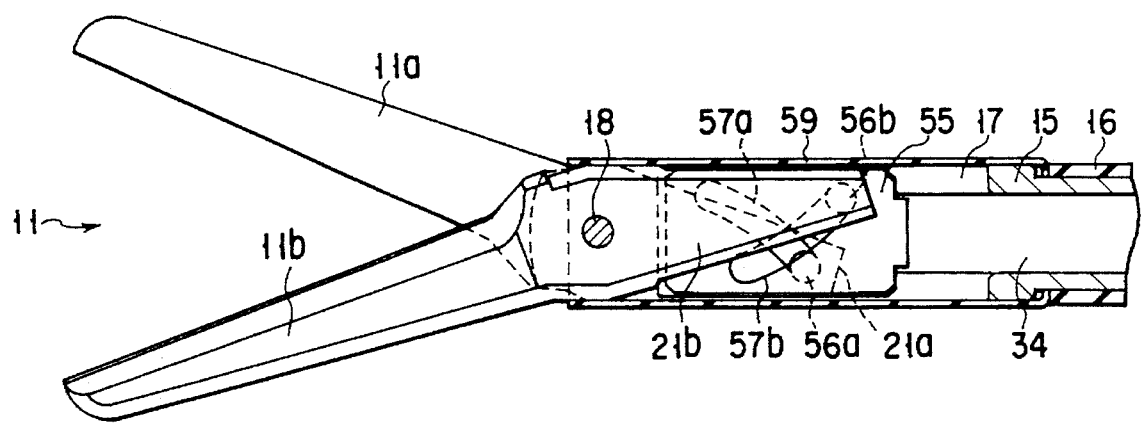
F I G. 8

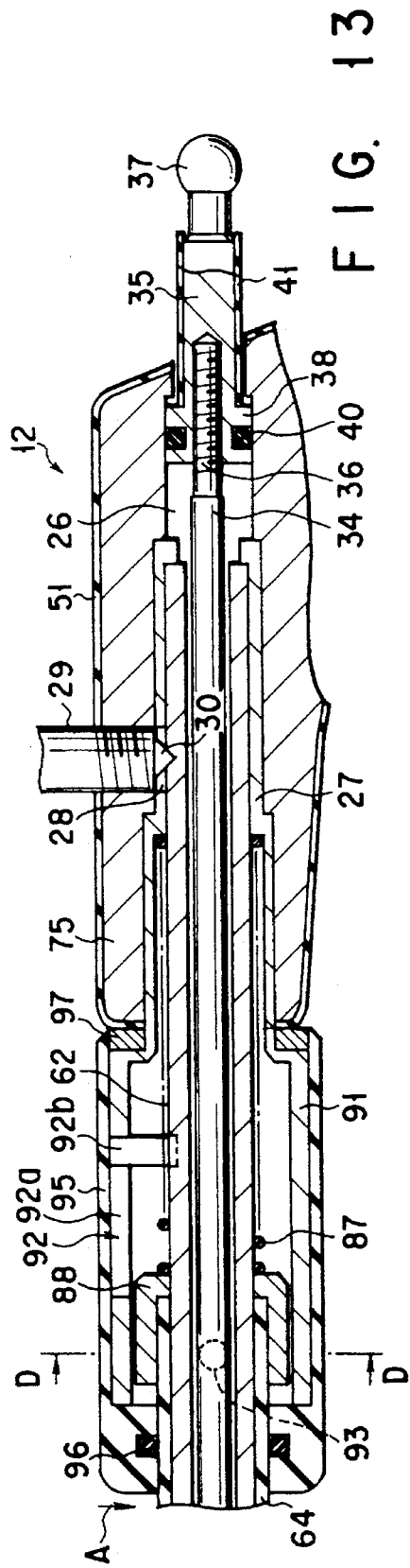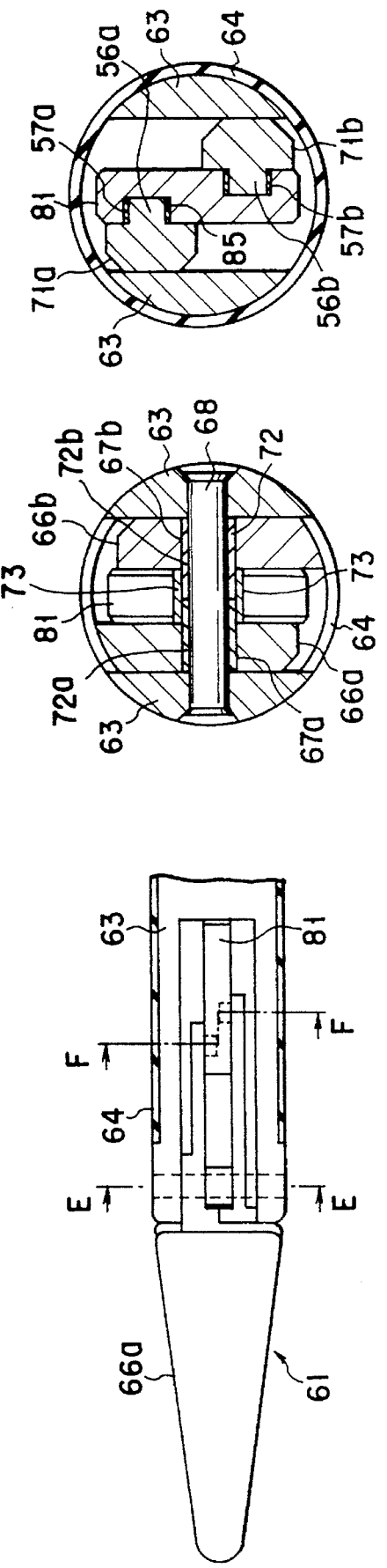

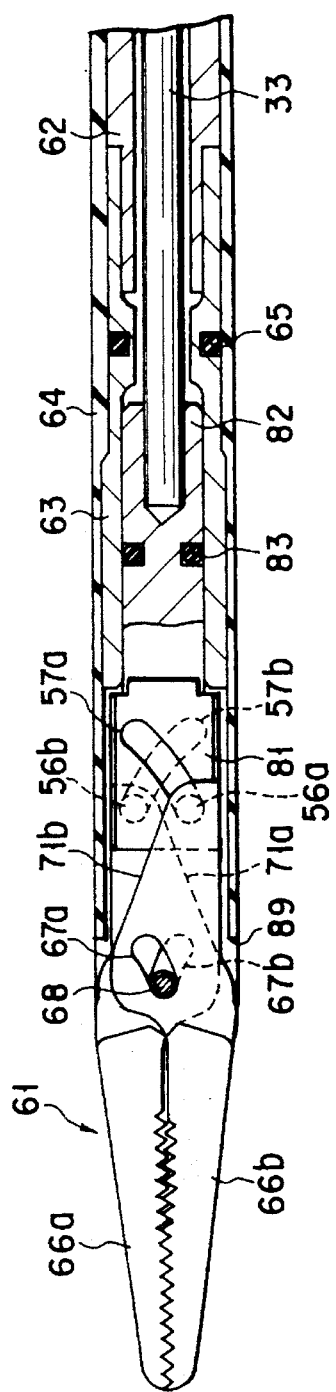
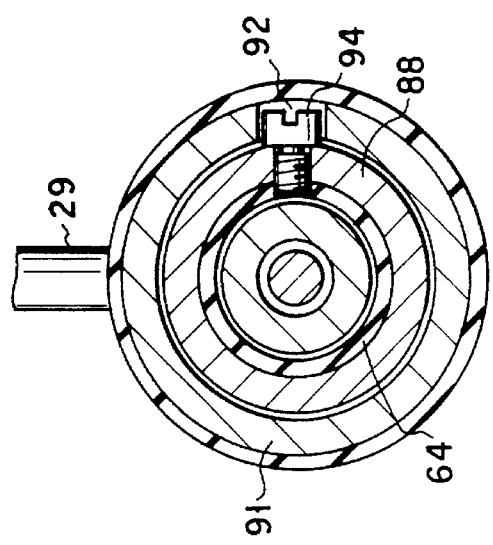
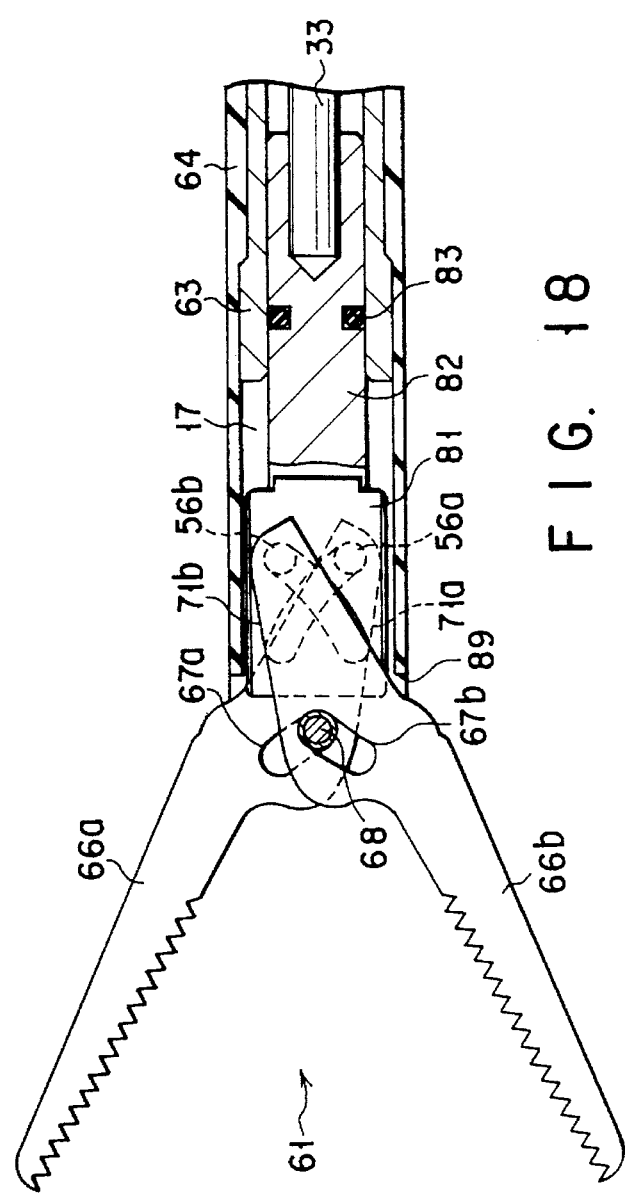
FIG. 17
FIG. 19
FIG. 18

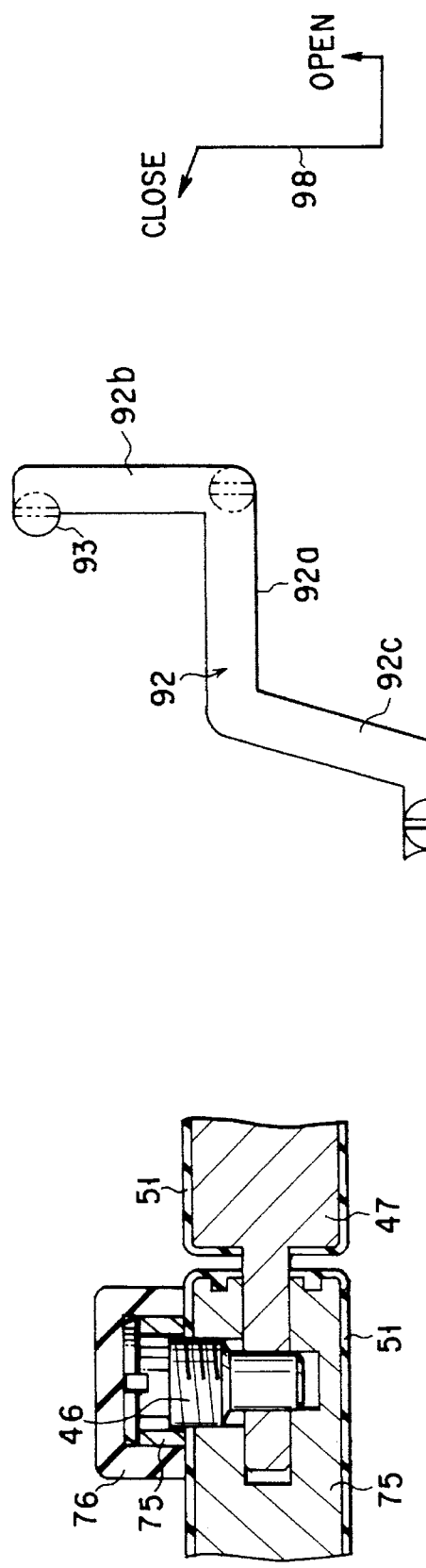
FIG. 20
FIG. 21
FIG. 22
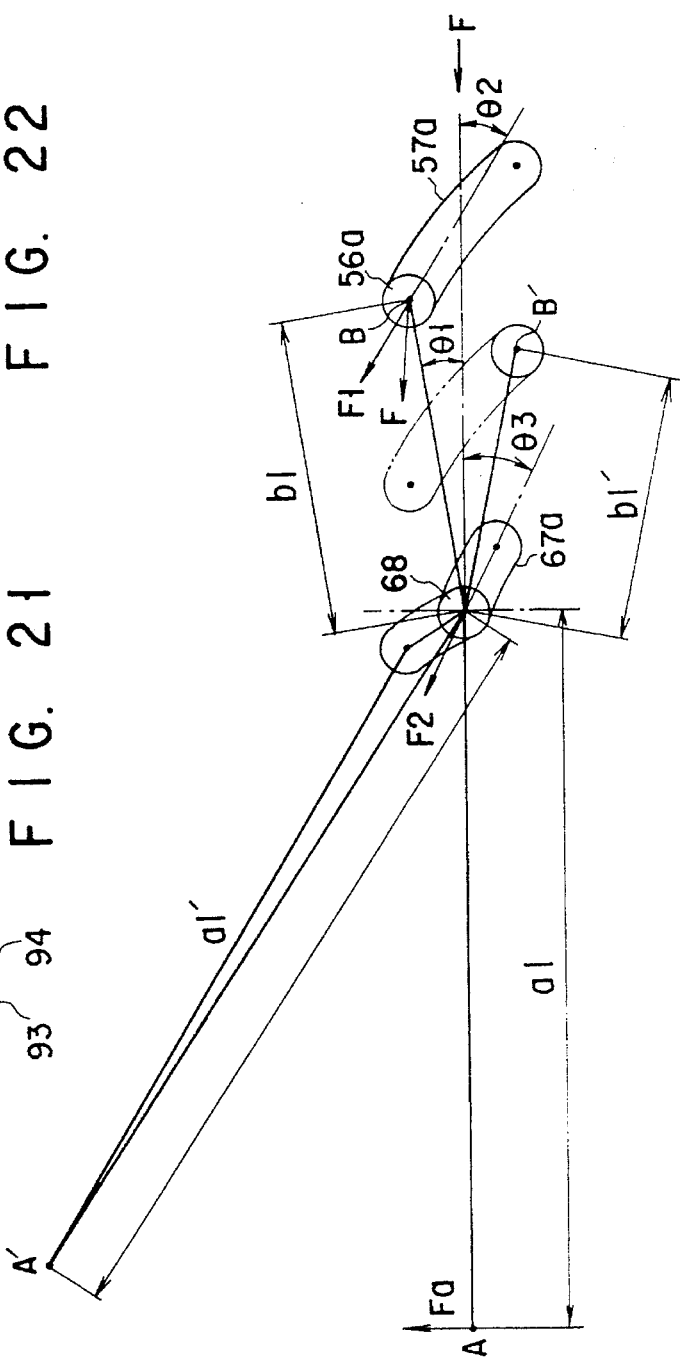
FIG. 23

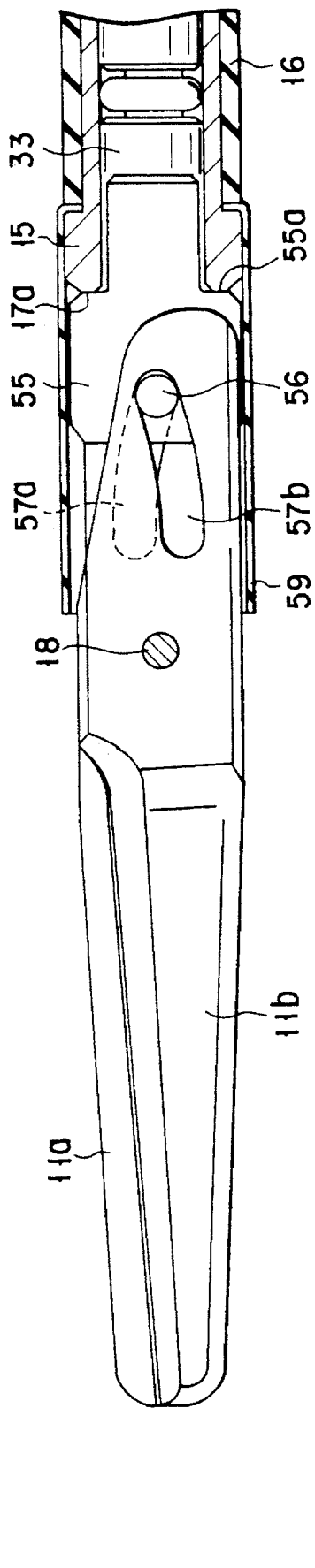
F I G. 29
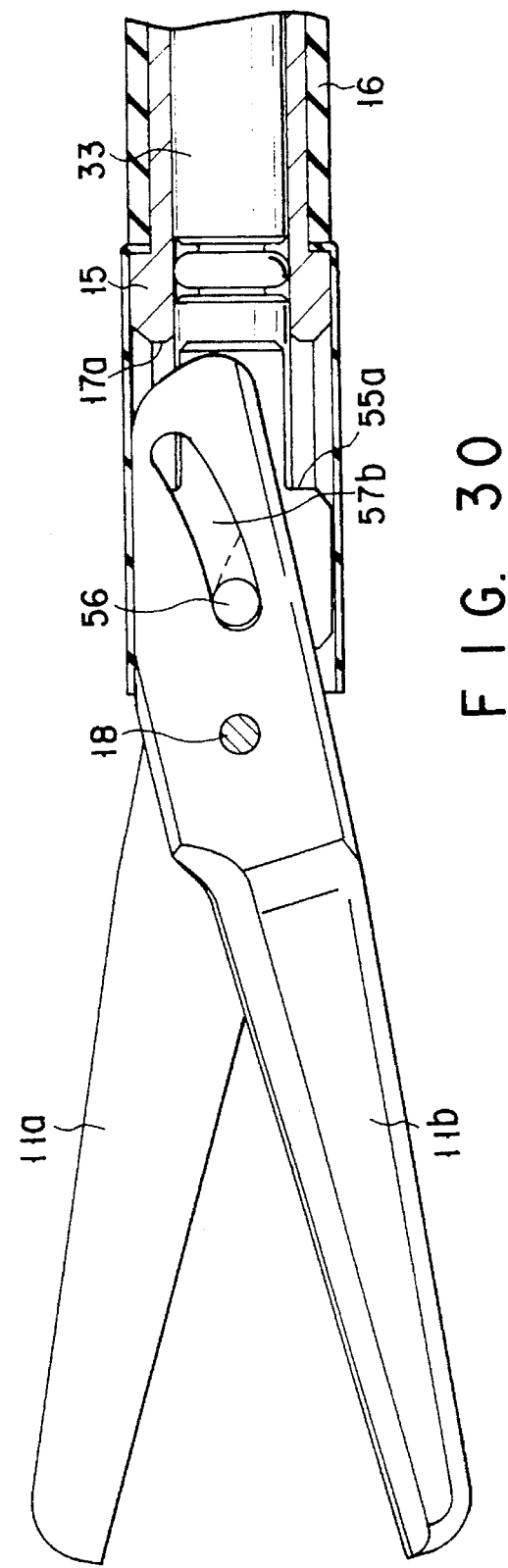
F I G. 30

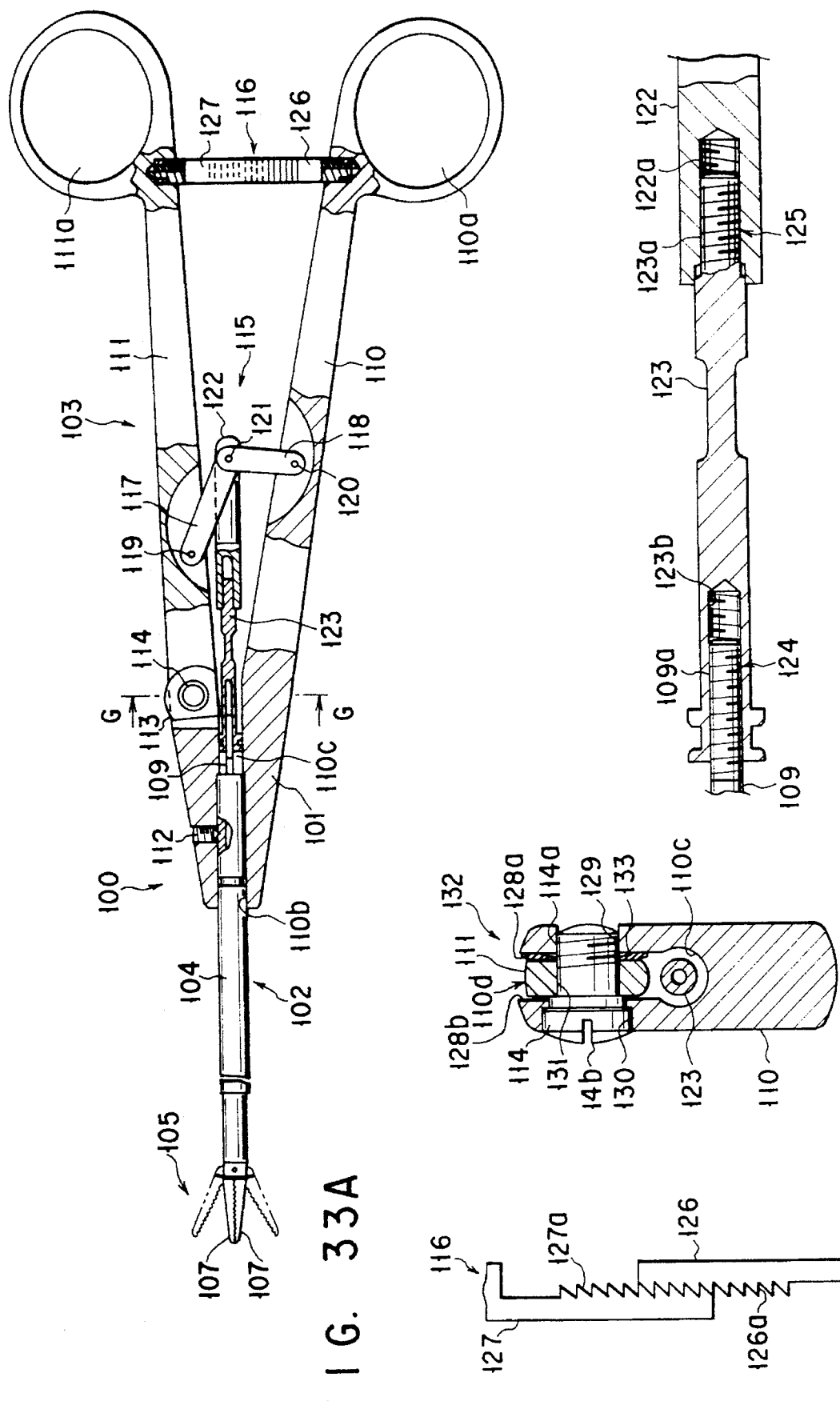
F I G. 33A
F I G. 33B
F I G. 33C
F I G. 33D

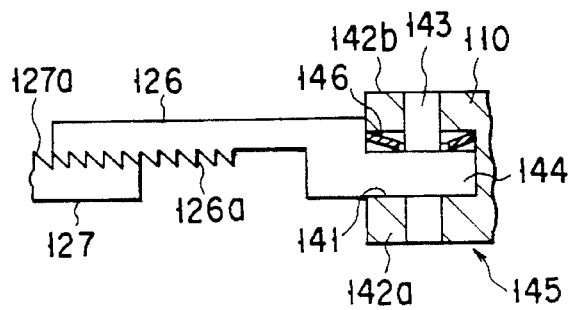
FIG. 34
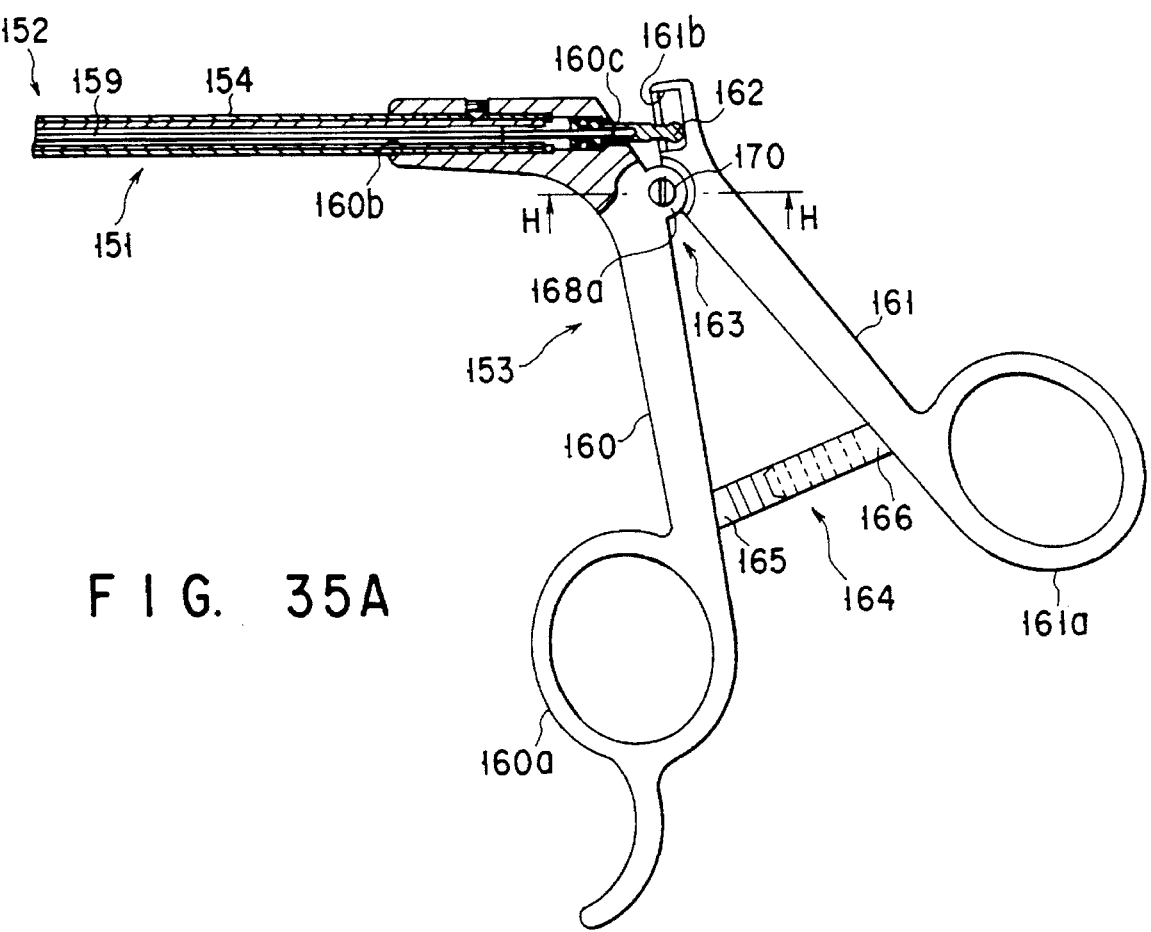
FIG. 35A
FIG. 35B
FIG. 35C

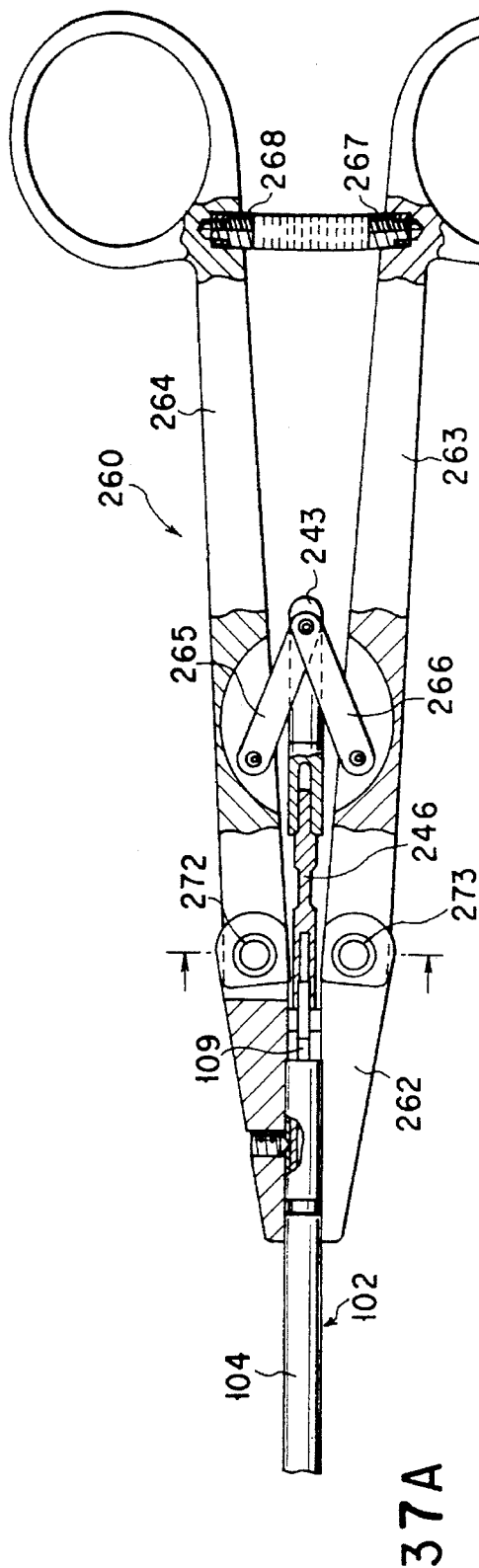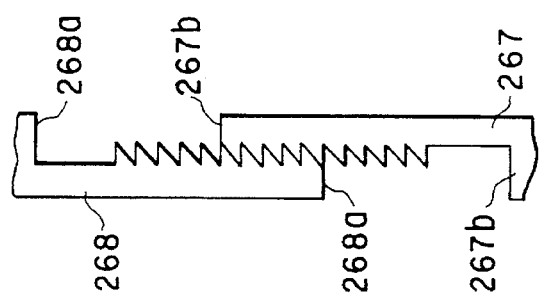
FIG. 37C
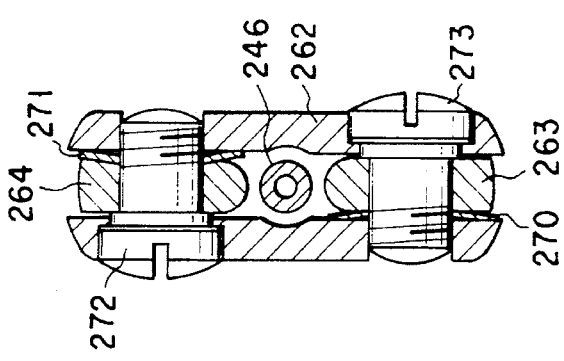
FIG. 37B
FIG. 37A

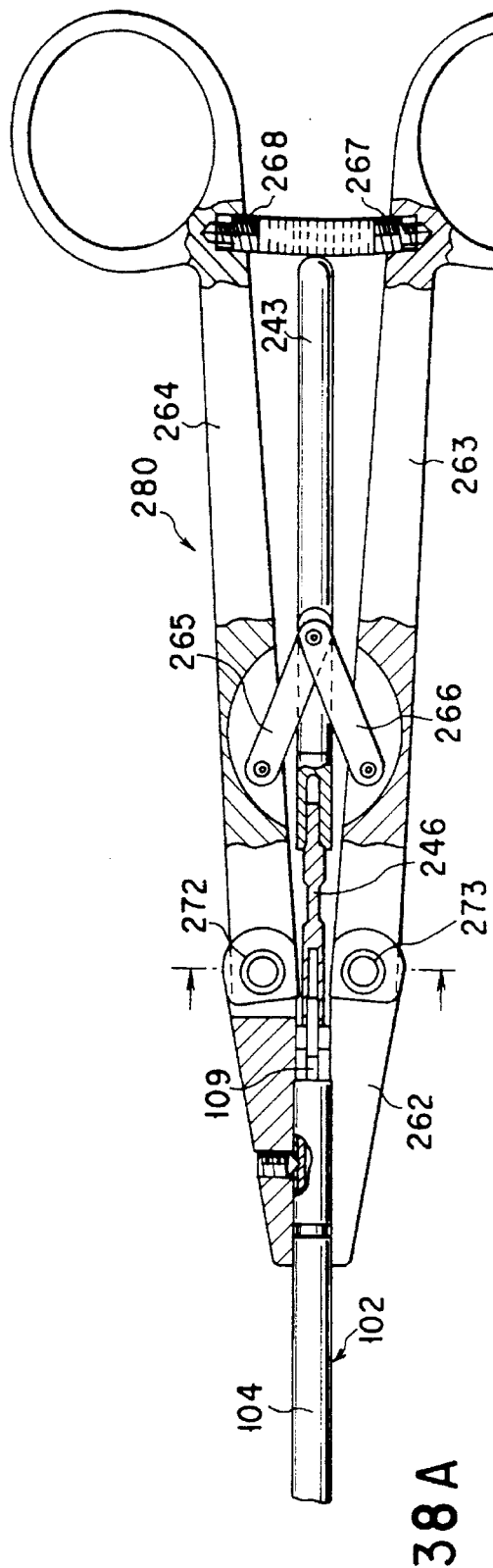
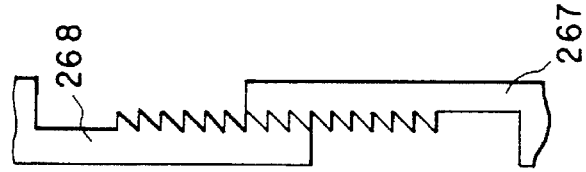
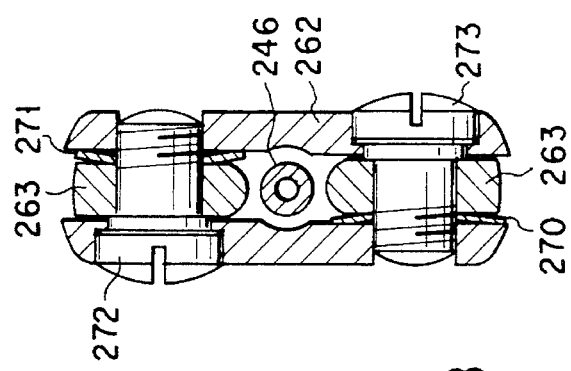
FIG. 38A
FIG. 38C
FIG. 38B

SURGICAL INSTRUMENT

BACKGROUND OF THE INVENTION

1. Field of the Invention

The present invention relates to a surgical instrument used to seize or cut tissue, for example, in an endoscopic surgical operation in the body cavity, such as laparoscopic surgery or surgery.

2. Description of the Related Art

Conventional forceps used to seize or cut tissue in an endoscopic surgical operation are described in Jpn. Pat. Appln. KOKAI Publication No. 4-246344 and EPO No. 484,671 A2. In these forceps, an openable forceps section is attached to the distal end of a body section having an outer tube and an operating section mounted on the proximal end of the outer tube. The outer tube is penetrated by a rod member. The forceps section is opened or closed by operating the operating section to move the rod member.

The forceps section is composed of a pair of forceps members which are rockable around a pivot pin, and a straight cam groove is formed in the rear end portion of each forceps member. Engaging pins, which are adapted to engage their corresponding cam grooves simultaneously, protrude from the distal end portion of the operating rod member. As the engaging pins move in association with the movement of the rod member, the forceps members swing around the pivot pin.

In a forceps for surgical operation described in West German Gebrauchsmuster (Utility Model) No. G8809501, a pair of forceps members rockable around a pivot pin and a movable guide member are attached to the distal end portion of a rod-shaped forceps body. An extension portion is provided on the rear end portion of each forceps member. The guide member is provided with guide channels in which the extension portions are inserted individually. The guide channels are formed as through holes which open on the distal end face and side face of the guide member. As the guide member is moved by means of the operating rod member, the extension portions of the forceps members are inserted into their corresponding guide channels to change the state of engagement, whereby the forceps members are opened or closed.

According to these forceps, however, when the forceps members are urged to open wide to cut tissue or seize an instrument or tissue, the rear end portions of the members inevitably project long beyond the diameter of the outer tube of an insertion section as the forceps body.

Each forceps of this type is passed through a cylindrical trocar when it is used. If you try to draw out the forceps with the rear end portions of the forceps members projecting from the body, therefore, the members are caught by the front end of the trocar, and cannot be easily closed. In delivering a suture into the body cavity in a manner such that it is twined around the outer tube, moreover, the suture is liable to be caught by the rear end portions of the forceps members projecting from the tube.

According to the latter forceps, the extension portions of the forceps members project long beyond the diameter of the insertion section through the guide channels when the forceps members are opened. Besides being subject to the aforesaid drawback, therefore, the forceps can be easily broken owing to the slenderness of their extension portions when the forceps section is left open, the extension portions project diagonally rearward. In this state, therefore, the extension portions may possibly be caught by the front end of the trocar, so that the forceps cannot be removed at once.

As an open-close mechanism for the forceps section, on the other hand, a four-joint parallel link mechanism may be arranged such that its two links are formed of the respective proximal end portions of the forceps members when the forceps members are opened wide, in this arrangement, however, the links project long beyond the diameter of the outer tube of the insertion section. With the forceps members left open in this manner, the forceps cannot be drawn out of the trocar. As is the case with the four-joint link mechanism, the force applied at the distal end portion is smallest when the forceps members are fully closed. Functionally, therefore, the mechanism of this type has a disadvantage that if its links are small in size, then the forceps' capability of seizing or cutting tissue is low. It is not advisable, therefore, to diminish the projection of the links by reducing the size of the links of the link mechanism. Thus, the links inevitably project long beyond the diameter of the outer tube of the insertion section when the forceps members are opened wide.

In cauterizing tissue in the body cavity by means of high-frequency current with use of the operative forceps of this type as a probe, moreover, there is a possibility of the projecting portions of the open-close mechanism touching and unexpectedly cauterizing some other regions outside a target region. Accordingly, an operator is expected to perform an operation carefully with a high technique.

Furthermore, some portions of the open-close mechanism for the forceps members project outside the diameter of the outer tube of the insertion section, and are bound to be exposed. In some cases, therefore, blood or other body fluids may get into the open-close mechanism, thereby hindering the open-close operation.

SUMMARY OF THE INVENTION

The object of the present invention is to provide a surgical instrument, in which no part of an open-close mechanism for operating an open-close member projects beyond the diameter of an insertion section as a forceps body when the forceps member is opened or closed, so that the mechanism neither obstructs the view of endoscopic observation nor catches a suture or any other fine things, in which the operating efficiency is improved so that the open-close mechanism for the open-close member can be easily inserted and removed without being caught by a trocar or the like, in which there is no possibility of the open-close mechanism touching and unexpectedly cauterizing any other regions outside a target region in the body cavity in cauterizing the target region by means of high-frequency current, and in which blood or other body fluids can be prevented from getting into the open-close mechanism and hindering its open-close operation.

In order to achieve the above object, according to the present invention, there is provided a surgical instrument for treatment in the body cavity, which comprises: an operating section including an operating handle; a sheath for an insertion section including a distal end portion to be inserted into the body cavity and a proximal end portion connected to the operating section; at least one open-close member for treatment pivotally mounted on the distal end portion of the sheath by means of a pivot pin; a cam mechanism connected to the open-close member, situated nearer to the proximal end of the sheath than the open-close member, and including a cam groove and a cam pin in engagement with the cam groove, so that the open-close member is rocked depending on the relationship between the pin and the groove, the component members of the cam mechanism having external shapes such that those portions on the proximal end side of the position near the pivot pin do not project from the sheath in every operating state; and a driving rod member passed through the sheath for reciprocation and having a front end connected to the cam mechanism and a rear end connected to the operating section, the cam mechanism being activated to open and close the open-close member for treatment as the rod member is moved by means of the operating handle.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a side view showing an outline of a forceps according to a first embodiment of the present invention;

FIG. 2 is a sectional view showing the principal part of an operating section of the forceps;

FIG. 7 is a sectional view showing the distal end portion of the forceps and its surroundings;

FIG. 8 is a sectional view showing the distal end portion of the forceps and its surroundings with forceps members open;

FIG. 13 is a sectional view showing the principal part of an operating section of the forceps according to the fifth embodiment;

FIG. 14 is a plan view showing a distal end portion of the forceps according to the fifth embodiment and its surroundings;

FIG. 15 is a sectional view taken along line E—E of FIG. 14;

FIG. 16 is a sectional view taken along line F—F of FIG. 14;

FIG. 17 is a sectional view of an insertion section of the forceps according to the fifth embodiment;

FIG. 18 is a sectional view of the insertion section of the forceps according to the fifth embodiment with forceps members open;

FIG. 19 is a sectional view taken along line D—D of FIG. 13;

FIG. 20 is a sectional view taken along line C—C of FIG. 12;

FIG. 21 shows a development of the configuration of a retaining hole of the forceps according to the fifth embodiment;

FIG. 22 is a diagram showing an index formed on an insulating cover of the forceps according to the fifth embodiment;

FIG. 23 is a diagram illustrating the principle of operation of a cam mechanism for driving a forceps according to a sixth embodiment of the invention;

FIG. 29 is a sectional view showing a distal end portion of a forceps according to another modification of the first embodiment and its surroundings;

FIG. 30 is a sectional view showing the open-state distal end portion of the forceps according to the second modification of the first embodiment and its surroundings;

FIG. 33A is a sectional view of a forceps according to an eighth embodiment of the invention;

FIG. 33B is a side view showing a state of engagement between engaging members of a retaining portion according to the eighth embodiment;

FIG. 33C is a sectional view taken along line G—G of FIG. 33A;

FIG. 33D is a longitudinal sectional view showing a length adjusting mechanism according to the eighth embodiment;

FIG. 34 is a side view showing a state of engagement between engaging members of a retaining portion according to a ninth embodiment;

FIG. 35A is a sectional view of a forceps according to a tenth embodiment of the invention;

FIG. 35B is a sectional view of a support portion for a retaining portion according to the tenth embodiment;

FIG. 35C is a side view showing a state of engagement between engaging members of the retaining portion;

FIG. 37A is a sectional view of an operating section of a forceps according to a twelfth embodiment of the invention;

FIG. 37B is a sectional view of a support portion for a retaining portion according to the twelfth embodiment;

FIG. 37C is a side view showing a state of engagement between engaging members of the retaining portion;

FIG. 38A is a sectional view of an operating section of a forceps according to a thirteenth embodiment of the invention;

FIG. 38B is a sectional view of a support portion for a retaining portion according to the thirteenth embodiment; and FIG. 38C is a side view showing a state of engagement between engaging members of the retaining portion.

DETAILED DESCRIPTION OF THE PREFERRED EMBODIMENTS

Figure 3:
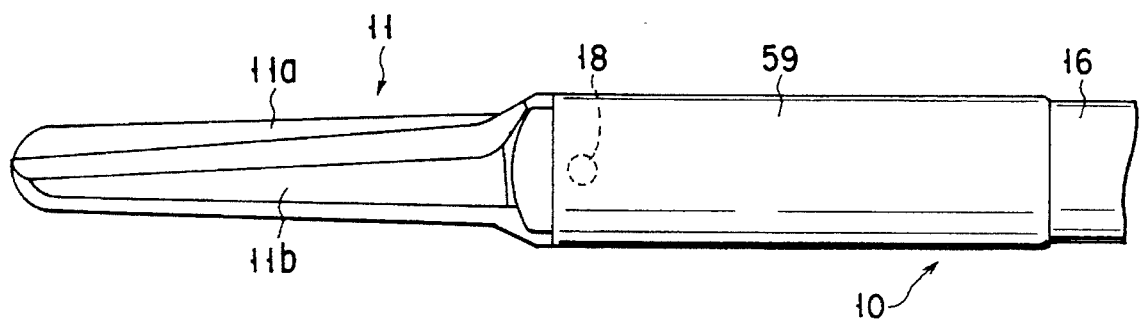
FIG. 3 is a side view showing a distal end portion of the forceps and its surroundings.
Figure 4:
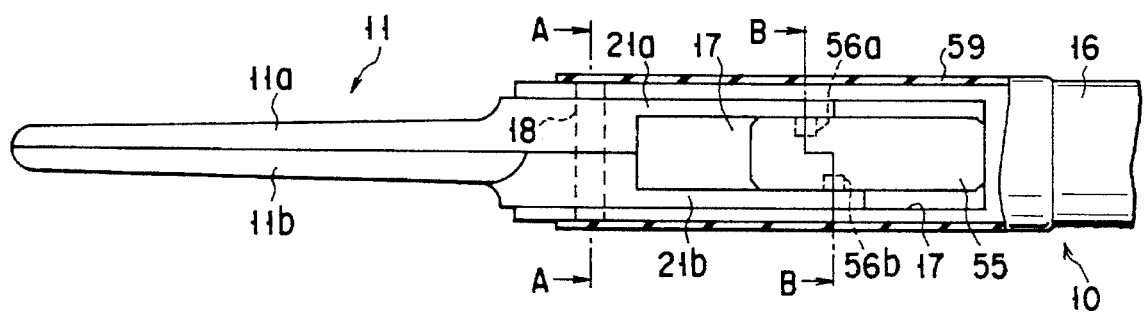
FIG. 4 is a plan view showing the distal end portion of the forceps and its surroundings.

Referring now to FIGS. 1 to 8, a first embodiment of the present invention will be described.

FIG. 1 shows an outline of a scissors-type surgical forceps. In FIG. 1, numeral 10 denotes an insertion section which is adapted to be inserted into the body cavity, such as the abdominal cavity, through the bore of a guide instrument, such as an endoscope or trocar. A forceps section 11 (scissors) for cutting the tissues of internal organs, blood vessels, etc. in the body cavity is attached to the distal end of the insertion section 10, and an operating section 12 is provided at the proximal end of the section 12.

As shown FIGS. 2 to 8, the insertion section 10 includes a electrically conductive tubular sheath 15 which is formed of a metallic material, such as stainless steel. The outer surface of the sheath 15 is covered by an electrically insulating tubular cover 16.

The distal end portion of the sheath 15, which is fitted with the forceps section 11, constitutes a slitted portion 17. The forceps section 11 includes a pair of forceps members 11a and 11b as open-close members for treatment formed of a metallic material, such as stainless steel. Each of the members 11a and 11b has a through hole in its middle portion. A support pin 18 is passed through the respective through holes of the forceps members 11a and 11b, whereby the members 11a and 11b are supported for rotation. The opposite end portions of the pin 18 are fixed individually to the right- and left-hand walls of the distal slitted portion 17. Rear-end arm portions 21a and 21b of the forceps members 11a and 11b are located in the slitted portion 17 so as to be rockable within the range of the internal space of the portion 17.

As shown in FIG. 2, on the other hand, the operating section 12 is formed having a rod passage hole 26 which penetrates its body 25 so as to be coaxial with the insertion section 10. The diameter of the front end portion of the hole 26 is larger than that of the rear end portion. The proximal end portion of the insertion section 10 is fitted in the wider front end portion of the hole 26. An abutting pipe 27 is fitted on the proximal end portion of the insertion section 10. A notched hole 28 is formed in part of the side wall of the middle portion of the pipe 27.

An electrode pin 29 for connection with a high-frequency power source is screwed in the operating section body 25. A conical retaining projection 30 is formed on the distal end of the pin 29. The retaining projection 30 penetrates the notched hole 28 of the abutting pipe 27, engages a V-shaped depression in the sheath 15 of the insertion section 10, and runs directly against the sheath 15, thereby clamping the sheath 15. As a result, the electrode pin 29 is connected also electrically to the sheath 15, so that a high-frequency current supplied from the high-frequency power source (not shown) through the pin 29 can be supplied to the forceps members 11a and 11b of the forceps section 11 through the sheath 15. This forceps may also be used as a probe for high-frequency treatment.

A driving rod member 33 is passed through the sheath 15 of the insertion section 10 and the rod passage hole 26. The rod member 33 is composed of a rod body 34 and a connecting rod 35 which are connected to each other. The body 34 and the rod 35 are connected by screwing the rod 35 onto a thread portion 36 formed on the proximal end portion of the body 34. As shown in FIG. 2, the rear end portion of the connecting rod 35 projects from the rear end portion of the operating section body 25, and the projecting end is formed as a spherical portion 37. The portion 37 constitutes a terminal which connects the rod body 34 to operating handles (mentioned later).

The front end portion of the connecting rod 35 constitutes a large-diameter portion 38. The portion 38 is designed so that its front end runs against the rear end face of the abutting pipe 27 when the driving rod member 33 is advanced, and that its rear end runs against a stepped portion 39 at the narrower rear end portion of the rod passage hole 26 when the member 33 is retreated. Thus, the stroke of the rod member 33 is defined between the rear end face of the pipe 27 and the stepped portion 39.

An O-ring 40 is provided on the peripheral surface of the large-diameter portion 38 of the connecting rod 35. A heat-shrinkable tube 41, which is formed of an electrically insulating material, such as fluoroplastics, is fitted on the outer peripheral surface of the rod 35.

The operating section body 25 is provided with a fixed or stationary operating handle 45 and a rockable operating handle 47 which is rockably mounted on the body 25 by means of a setscrew pin 46. Finger ring portions 48 and 49 are formed on the operating end portions of the handles 45 and 47, respectively. The respective outer surfaces of the operating section body 25 and the handles 45 and 47 are coated with an insulating film 51 which serves to prevent an electric shock attributable to the high-frequency current.

A vertically elongated engaging groove 52 is formed in the operating end of the rockable operating handle 47. The spherical portion 37 of the driving rod member 33 is fitted in the groove 52. As the handle 47 is rocked, the rod member 33 moves in the sheath 15 of the insertion section 10.

Figure 6:
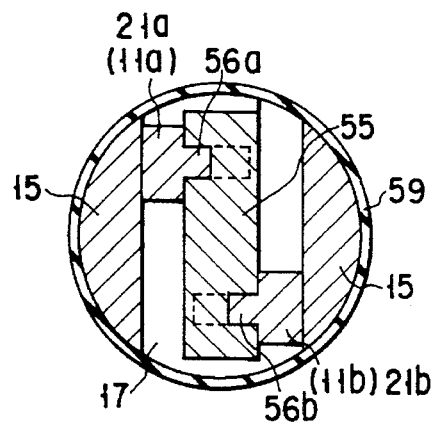
FIG. 6 is a sectional view taken along line B—B of FIG. 4.

The following is a description of the construction of a cam mechanism for operating the forceps section 11. A forceps operating member 55 is attached to the distal end of the rod body 34. As shown in FIG. 6, the member 55 is situated between the rear-end arm portions 21a and 21b of the forceps members 11a and 11b in the center of the inside space of the distal slitted portion 17. The arm portions 21a and 21b are provided with cam pins 56a and 56b, respectively, which project toward the side faces of the forceps operating member 55. As shown in FIGS. 7 and 8, arcuate cam grooves 57a and 57b, which are inclined in nonparallel relation with respect to the moving direction of the driving rod member 33, are formed individually in the opposite side faces of the member 55.

A combination of the cam groove 57a and the cam pin 56a and a combination of the groove 57b and the pin 56b are deviated from each other in the longitudinal direction. Although the slanting cam grooves 57a and 57b intersect each other, as shown in FIGS. 7 and 8, the cam pins 56a and 56b moving in the forceps section 11 during open-close operation pass the point of intersection with a time lag due to the deviation. Even if the cam grooves 57a and 57b are designed so as to overlap each other in their depth direction, as indicated by broken lines in FIG. 6, therefore, the cam pins 56a and 56b never interfere with each other with the grooves 57a and 57b thus overlapping each other in the depth direction, the depth of engagement between the pins 56a and 56b and the grooves 57a and 57b can be increased. Moreover, the thickness of the member 55 may be reduced to make the cam mechanism more compact with respect to the depth direction of the cam grooves 57a and 57b.

As the cam pins 56a and 56b move relatively to each other in their corresponding cam grooves 57a and 57b, as shown in FIG. 6, the forceps members 11a and 11b swing around the support pin 18 for open-close operation, as shown in FIGS. 7 and 8.

Figure 5:
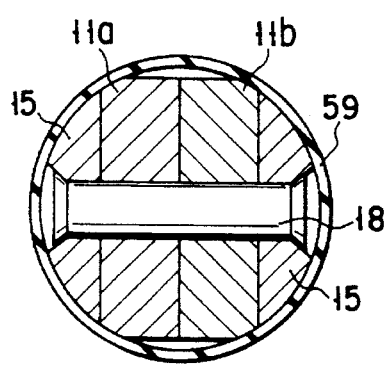
FIG. 5 is a sectional view taken along line A—A of FIG. 4.

The members 21a, 21b, 55, 56a and 56b of the cam mechanism are arranged so as to be always situated within the region of the insertion section 10, as shown in FIGS. 5 and 6. Thus, the respective configurations of the rear-end arm portions 21a and 21b, cam pins 56a and 56b, and cam grooves 57a and 57b are rationally set in consideration of their functions. These component members of the cam mechanism have external shapes such that they never project from the sheath 15 in every operating state.

Since the individual members of the cam mechanism are thus arranged so as to be always situated within the region of the insertion section 10, they can be covered compactly. More specifically, a tubular distal cover 59 is provided adjacent to the distal end of the insulating cover 16 so as to cover the slitted portion 17 at the distal end of the sheath 15. The distal cover 59 is formed of an electrically insulating material. The rear end of the cover 59 is turned inward so as to abut against the distal end of the insulating cover 16. The distal end of the cover 59 is situated ahead of the position near the support pin 18. Actually, the distal end of the distal cover 59 is situated ahead of the position of the pin 18, as shown in FIGS. 7 and 8.

The cam grooves 57a and 57b are not limited to the arcuate configuration, and may be inclined in a straight line or some other curved line. As shown in FIGS. 7 and 8, the grooves 57a and 57b are each in the form of an inwardly convex arc. This arc is designed so that the angles of inclination of those slopes of the grooves 57a and 57b which are touched by the cam pins 56a and 56b are constant when the forceps operating member 55 is moved to open or close the forceps section 11. The driving force for the forceps section 11 is fixed without being changed according to the opening of the section 11. Naturally, however, this driving force may be set so as to vary depending on the opening of the forceps section 11 by alternatively shaping the cam grooves 57a and 57b. If the grooves 57a and 57b are straight, the wider the opening of the forceps section 11, the smaller the driving force is. If the grooves 57a and 57b are each in the form of an outwardly convex arc, the driving force tends to be drastically reduced as the forceps section 11 opens.

In the embodiment arranged in this manner, the cam mechanism for open-close operation is constructed as follows. The arcuate cam grooves 57a and 57b, which are inclined in different directions with respect to the moving direction of the driving rod member 33, are arranged individually in the side faces of the forceps operating member 55 at the distal end of the rod member 33 in nonparallel relation. Moreover, the cam pins 56a and 56b, which are individually in engagement with the grooves 57a and 57b, are formed on the proximal end portions of the rear-end arm portions 21a and 21b of the forceps members 11a and 11b, respectively. Accordingly, the forceps members 11a and 11b can be opened or closed without causing the mechanical parts for operating the members 11a and 11b to project from the lateral portion of the insertion section 10. Thus, the mechanical parts for open-close operation can be prevented from being caught by the guide instrument, such as the endoscope or trocar, as the insertion section 10 is drawn out from the body cavity. Further, the mechanical parts never obstruct the view in the body cavity observed through the endoscope, and cannot be caught by a suture or any other elongate things. In cauterization, moreover, there is no possibility of any parts touching and cauterizing any other regions outside a target region. In consequence, the operating efficiency is improved. Furthermore, the insulating distal cover 59 can compactly cover the distal end portion of the sheath 15, so that the high-frequency current can be securely prevented from leaking from the distal end portion of the sheath 15.

When the suture is delivered into the body cavity in a manner such that it is twined around an outer tube of the insertion section 10, the operating mechanism never projects from the outer tube, so that the suture cannot be easily caught by the mechanism. Thus, with use of the cover 59, the suture can be securely prevented from hitching.

Since the operating mechanism for operating the forceps members 11a and 11b never projects from the lateral portion of the sheath 15, moreover, the distal end portion of the sheath 15 can be compactly covered by means of the tubular distal cover 59. Accordingly, blood or other body fluids can be prevented from getting into the distal end portion of the sheath 15 and adhering to the cam grooves 57a and 57b of the forceps operating member 55 or the cam pins 56a and 56b. Thus, smooth steady operation of the operating mechanism for open-close operation can be secured.

In the embodiment described above, moreover, the open-close mechanism for operating the forceps members 11a and 11b, which is composed of the cam grooves 57a and 57b and the cam pins 56a and 56b in engagement with the grooves 57a and 57b, respectively, can be incorporated compactly in the system.

Since the pin 18 for supporting the forceps members 11a and 11b is concealed under the distal cover 59, furthermore, it can be prevented from slipping out of the sheath 15.

Figure 9:
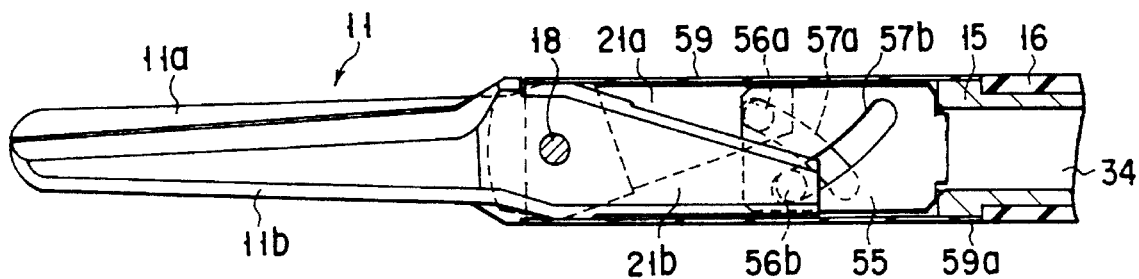
FIG. 9 is a sectional view showing a distal end portion of a forceps according to a second embodiment of the invention and its surroundings.

FIG. 9 shows a second embodiment of the present invention. In this embodiment, a rear end 59a of the distal cover 59 abuts straight against the front end of the insulating cover 16 without being turned inward. The respective front ends of the cam grooves 57a and 57b are opened forward at the distal end of the member 55. According to this arrangement, the cam pins 56a and 56b can be easily fitted into the cam grooves 57a and 57b of the member 55. The other components are arranged in the same manner as in the first embodiment.

Figure 10:
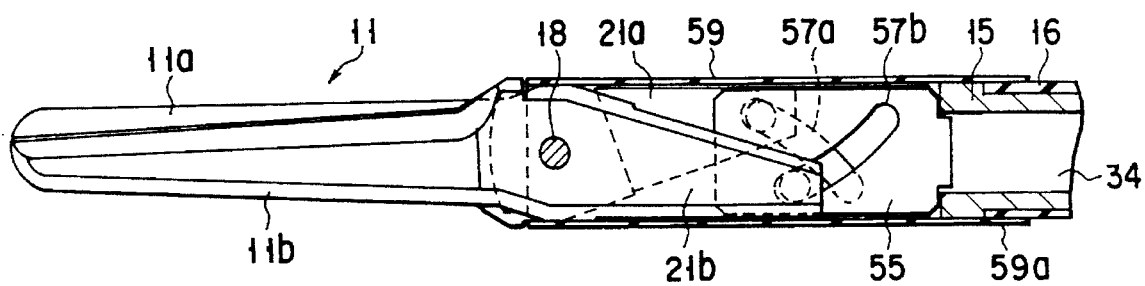
FIG. 10 is a sectional view showing a distal end portion of a forceps according to a third embodiment of the invention and its surroundings.

FIG. 10 shows a third embodiment of the present invention. In this embodiment, the rear end portion 59a of the distal cover 59 is lapped on the front end portion of the insulating cover 16 so as to conceal it. The other components are arranged in the same manner as in the first embodiment.

Figure 11:
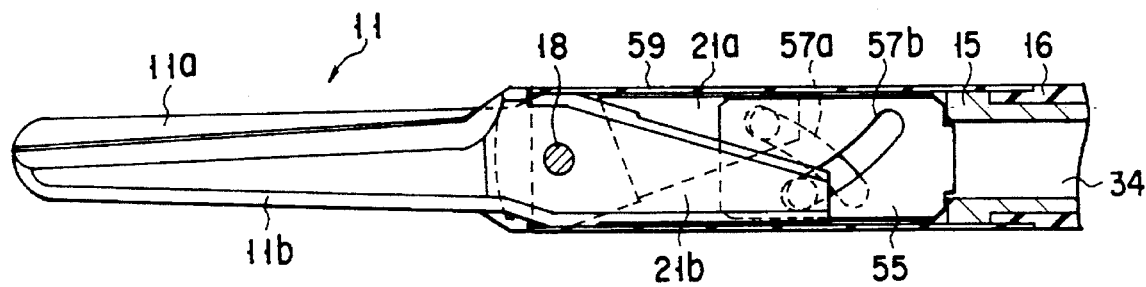
FIG. 11 is a sectional view showing a distal end portion of a forceps according to a fourth embodiment of the invention and its surroundings.

FIG. 11 shows a fourth embodiment of the present invention. In this embodiment, the front end portion of the insulating cover 16 is pressed into the rear end portion of the distal cover 59.

Figure 12:
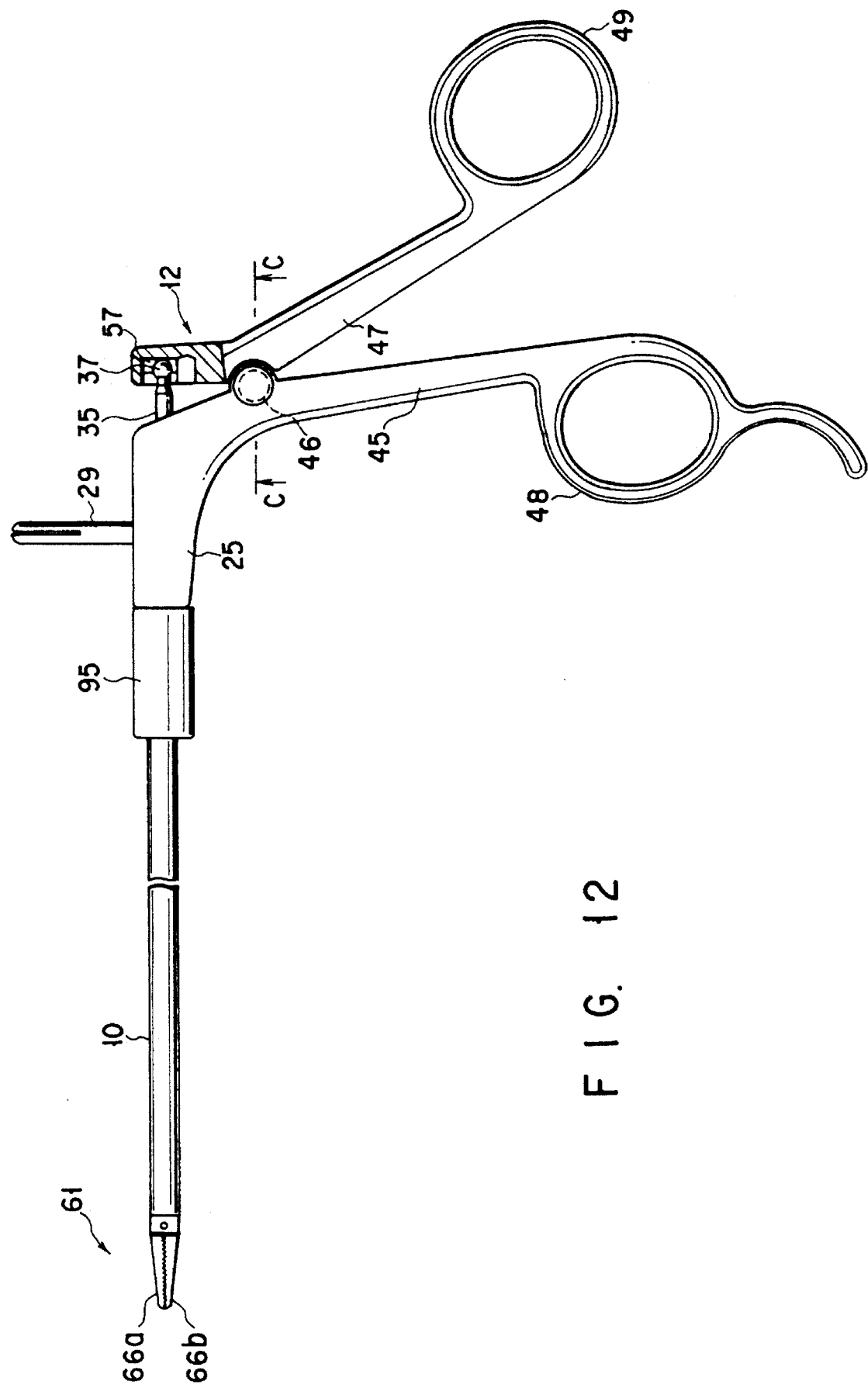
FIG. 12 is a side view showing an outline of a forceps according to a fifth embodiment of the invention.

Referring now to FIGS. 12 to 23, a fifth embodiment of the present invention will be described. FIG. 12 shows an outline of a seizing forceps for use as a surgical forceps. In FIG. 12, numeral 10 denotes an insertion section which is adapted to be inserted into the body cavity through a guide instrument, such as an endoscope or trocar. A seizing section 61 (forceps section) for seizing tissues in the body cavity is attached to the distal end of the insertion section 10. As shown in FIGS. 13 and 17, the insertion section 10 includes a tubular first sheath 62 formed of a metallic material, such as stainless steel, and a second sheath 63 fitted on the distal end of the first sheath 62. The sheaths 62 and 63 are covered by a tubular insulating cover 64 for electrical insulation. An O-ring 65, formed of a sealing material such as rubber, is provided on the outer peripheral surface of the second sheath 63.

As shown in FIGS. 14 to 17, the seizing section 61 includes a pair of forceps members 66a and 66b formed of a metallic material, such as stainless steel, and pin fitting holes 67a and 67b are formed in the middle portions of the members 66a and 66b, respectively. A support pin 68 is passed through the holes 67a and 67b, and its opposite ends are caulked and fixed individually to the right- and left-hand walls of a slitted portion 69 at the distal end portion of the sheath 63.

The proximal end portions of the forceps members 66a and 66b constitute arm portions 71a and 71b, respectively. The pin fitting holes 67a and 67b are oval in shape so that the forceps members 66a and 66b can be opened wide enough. Collars 72a and 72b are fitted on the support pin 68, and a ring 73 is fitted on the collars 72a and 72b. As shown in FIG. 15, the ring 73 is sandwiched between the forceps members 66a and 66b. The collars 72a and 72b are used to reduce friction.

The seizing section 61 is remotely operated by means of an operating section 12, which is attached to the proximal end of the insertion section 10, through the medium of a cam mechanism, which will be mentioned later. The operating section 12, as shown in FIG. 13, is constructed basically in the same manner as the one according to the first embodiment. Like reference numerals are used to designate like portions, and a detailed description of those portions is emitted. Also, the driving rod member 33 is constructed in like manner.

As shown in FIG. 20, an insulating cap 76 is fitted on the head of a setscrew pin 46 for pivotally supporting the rockable operating handle 47, with the aid of a ring-shaped washer 75.

As the rockable operating handle 47 rocks, the driving rod member 33 moves in the sheaths 62 and 63. As shown in FIGS. 14 and 17, a forceps operating member 81 is attached to the distal end of the rod member 33 by means of a connecting shaft 82. An O-ring 83 is provided on the outer peripheral surface of the shaft 82 so as to be in sliding contact with the inner surface of the sheath 63.

The forceps operating member 81 is used to open and close the forceps members 66a and 66b. As shown in FIG. 17, arcuate cam grooves 57a and 57b, which are inclined in nonparallel relation with respect to the moving direction of the driving rod member 33, are formed individually in those side face portions of the operating member 81 which face the arm portions 71a and 71b of the forceps members 66a and 66b, respectively. As shown in FIG. 16, cam pins 56a and 56b on the arm portions 71a and 71b of the members 66a and 66b are fitted in the grooves 57a and 57b, respectively.

The pin fitting hole 67a in the forceps member 66a extends in the same direction as the cam groove 57a in which the cam pin 56a on the side of the member 66a is fitted. As shown in FIG. 18, therefore, the cam pins 56a and 56b move relatively to each other in their corresponding cam grooves 57a and 57b as the driving rod member 33 advances. Thereupon, the forceps members 66a and 66b swing around the pin 68 to open wide in a manner such that they move forward, guided by the pin fitting hole 67a.

A ring 85 for reducing the frictional resistance to each of the cam grooves 57a and 57b is loosely fitted on each of the cam pins 56a and 56b.

The distal end of the insulating cover 64 extends close to the pin 68 for supporting the forceps members 66a and 66b, thus covering pat of the cam mechanism for operating the forceps members.

The insulating cover 64 is movable in the axial and circumferential directions of the sheaths 62 and 63 which constitute the insertion section 10. As shown in FIG. 13, a cylindrical spring bearing member 88 for receiving the urging force of a coil spring 87 is mounted on the rear end of the cover 64. The function of the spring 87 is to press the distal end of the insulating cover 64 against a stepped portion 89 which is formed around the distal end portion of the second sheath 63. The coil spring 87, which is fitted on the first sheath 62, is situated between the abutting pipe 27 and the spring bearing member 88.

Formed on the front end of the abutting pipe 27 is a cylindrical large-diameter portion 91 which extends to the outside of the operating section body 25. The portion 91 is formed having a retaining hole 92 which regulates the range of movement of the insulating cover 64. As shown in FIG. 21, the retaining hole 92 includes a central portion 92a extending along the axis of the insertion section 10, a first retaining guide portion 92b extending vertically from the rear end of the central portion 92a, and a second retaining guide portion 92c extending diagonally forward from the front end of the central portion 92a. A retaining portion 93 is formed at the terminal portion of each of the retaining portions 92b and 92c.

As shown in FIG. 19, the head of a fixing screw 94 for fixing the spring bearing member 88 to the insulating cover 64 is fitted in the retaining hole 92. As the head of the screw 94 is moved from a full-line position shown in FIG. 21 to a broken-line position, the distal end of the cover 64 is locked in a position recessed from the distal end portion of the insertion section 10. The full-line position shown in FIG. 21 is a normal standby position in which the distal end of the insulating cover 64 abuts against the stepped portion 89.

A cylindrical insulating cover 95 is fitted on the front end of the operating section 12 so as to cover the large-diameter portion 91 at the front end of the abutting pipe 27. Seal rings 96 and 97 are arranged at the front and rear end portions, respectively, of the cover 95. Further, an index 98 is provided at the rear end portion (in the position indicated by arrow A in FIG. 13) of the cover 95. The index 98, which is shown in FIG. 22, indicates the way of retreating the cover 59 to expose the distal slitted portion 17 of the sheath 63.

According to the embodiment of the present invention arranged in this manner, the open-close mechanism for operating the forceps members 66a and 66b is composed of the forceps operating member 55 on the distal end of the driving rod member 33 and the cam pins 56a and 56b in engagement with the grooves 57a and 57b, respectively, formed in the side faces of the member 55. Therefore, the forceps members 66a and 66b of the seizing section 61 can be opened and closed without causing the component members of the cam mechanism for open-close operation to project from the lateral portion of the insertion section 10.

Since the distal slitted portion 17 of the insertion section 10 is covered by the cylindrical insulating cover 59, moreover, blood or other body fluids can be prevented from getting into the slitted portion 17 and adhering to the cam grooves 57a and 57b and the cam pins 56a and 56b which constitute the cam mechanism for opening and closing the forceps members 66a and 66b.

Since the pin fitting holes 67a and 67b of the forceps members 66a and 66b are in the form of ovals extending in the same directions as their corresponding cam grooves 57a and 57b, furthermore, the members 66a and 66b can advance along the holes 67a and 67b to widen their opening angle when the when they are opened.

Further, the ring 85 is rotatably fitted on each of the cam pins 56a and 56b which slide in the cam grooves 57a and 57b, respectively. Thus, the frictional resistance between the grooves 57a and 57b and the pins 56a and 56b can be reduced, so that the grooves and the pins can be prevented from being broken.

Since the cam grooves 57a and 57b are arcuate in shape, moreover, the cam pins 56a and 56b in engagement with the grooves 57a and 57b can move smoothly. Thus, the working resistance of the pins 56a and 56b in the grooves 57a and 57b can be lowered, so that the grooves and the pins can be prevented from being broken.

Since the insulating cover 64 for insulating the sheaths 62 and 63 is movable in the axial direction of the sheaths, furthermore, it can be moved toward the rear end of the sheath 63 to expose the distal end portion of the insertion section 10, thereby allowing blood or other body fluids adhering to the cam grooves 57a and 57b and the cam pins 56a and 56b to be washed away.

FIG. 23 is a diagram for illustrating the relationship between the cam groove 57a and the pin fitting hole 67a. In FIG. 23, a force $F_1$ acting in the tangential direction of the groove 57a is given by $F_1=F\cos\theta_2$, and a force $F_2$ acting in the tangential direction of the hole 67a by $F^2=F\cos\theta_1 \cos(\theta_3+\theta_1)$, where F is a force with which the driving rod member 33 pushes the forceps operating member 81, $\theta_1$ is an angle at which a line connecting a point B of application and an imaginary fulcrum C crosses the axis of the rod member 33, $\theta_2$ is an angle at which a tangent to the groove 57a crosses the axis of the member 33, and $\theta_3$ is an angle at which a tangent to the hole 67a crosses the axis of the member 33. The cam groove 57a is activated if $F_1>F_2$ is given, the groove 57a and the pin fitting hole 67a are activated simultaneously if we have $F_1=F_2$, and the hole 67a is activated if $F_1<F_2$ is given.

Since $F_1>F_2$ is given according to this embodiment, the cam groove 57a never fails to be activated first, and the pin fitting hole 67a is activated after the operation of the groove 57a is finished. The cam groove 57b and the pin fitting hole 67b are activated in like manner.

According to this arrangement, the oval slit is formed in each forceps member, and the support shaft is passed through the slits so that the forceps members are movable in the longitudinal direction of the insertion section. Thus, the opening angle of the forceps members can be widened.

Figure 24:
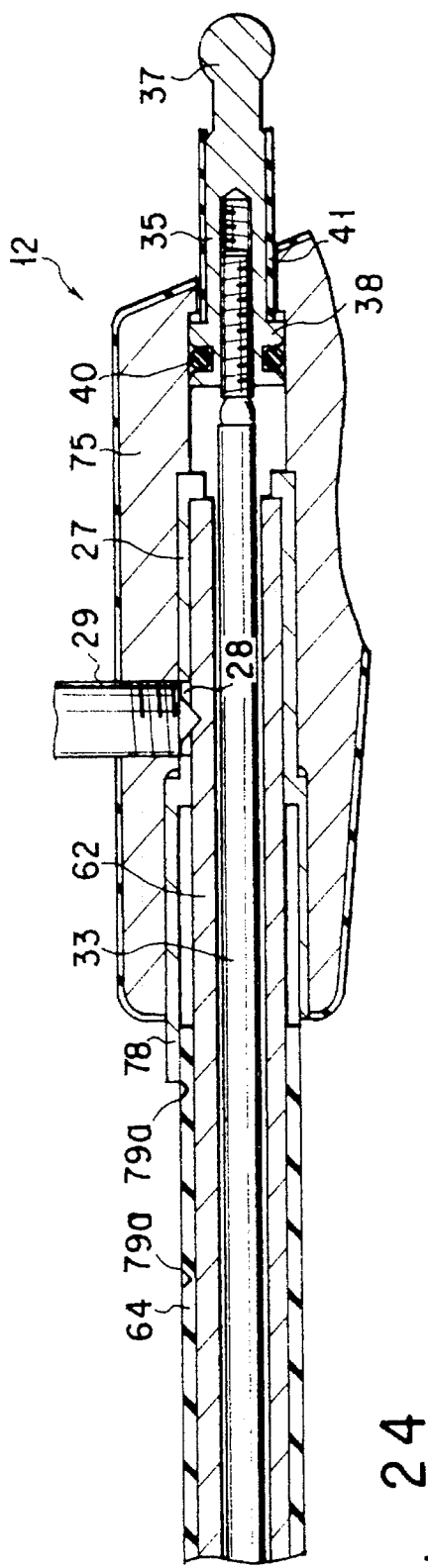
FIG. 24 is a sectional view showing the principal part of an operating section of a forceps according to a modification.
Figure 25:
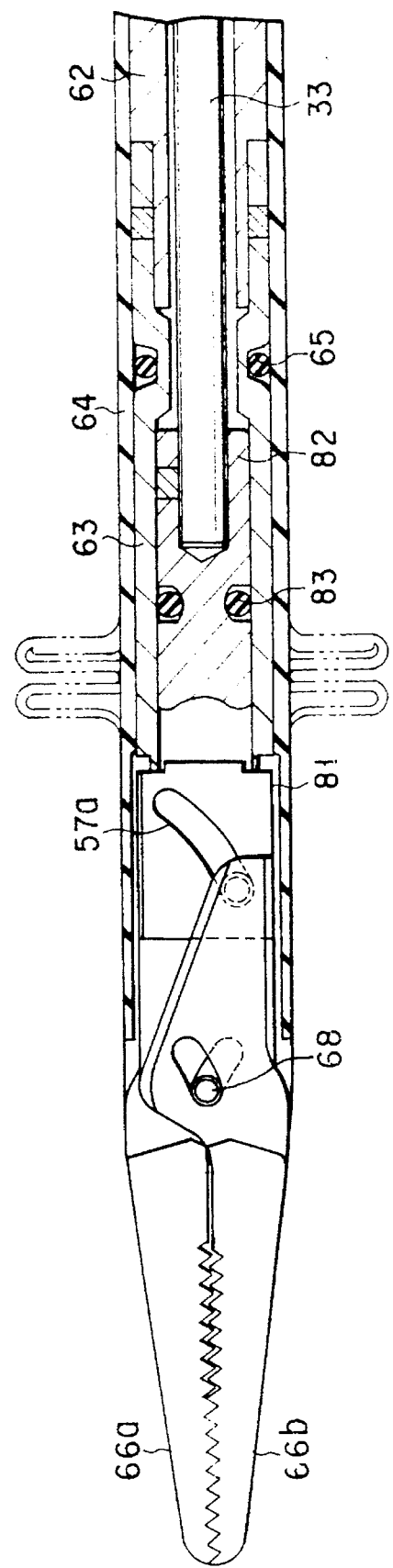
FIG. 25 is a sectional view of an insertion section of a forceps according to another modification.

The present invention is not limited to the embodiments described above. As shown in FIG. 24, for example, a retaining member 78 in the form of a leaf spring may be provided on the front end of the abutting pipe 27 so that the longitudinal position of the insulating cover 64 can be settled by causing the member 78 alternatively to engage one of click holes 79a and 79b formed in the insulating cover 64. Alternatively, the insulating cover 64 may be of a screw type such that the cover 64 and the first sheath 62 are formed individually having mating threaded portions. Alternatively, moreover, the insulating cover 64 may be formed of a flexible material such that its distal end can be transformed in the manner shown in FIG. 25 to be retreated from the distal slitted portion 17 of the first sheath 62.

Figure 26:
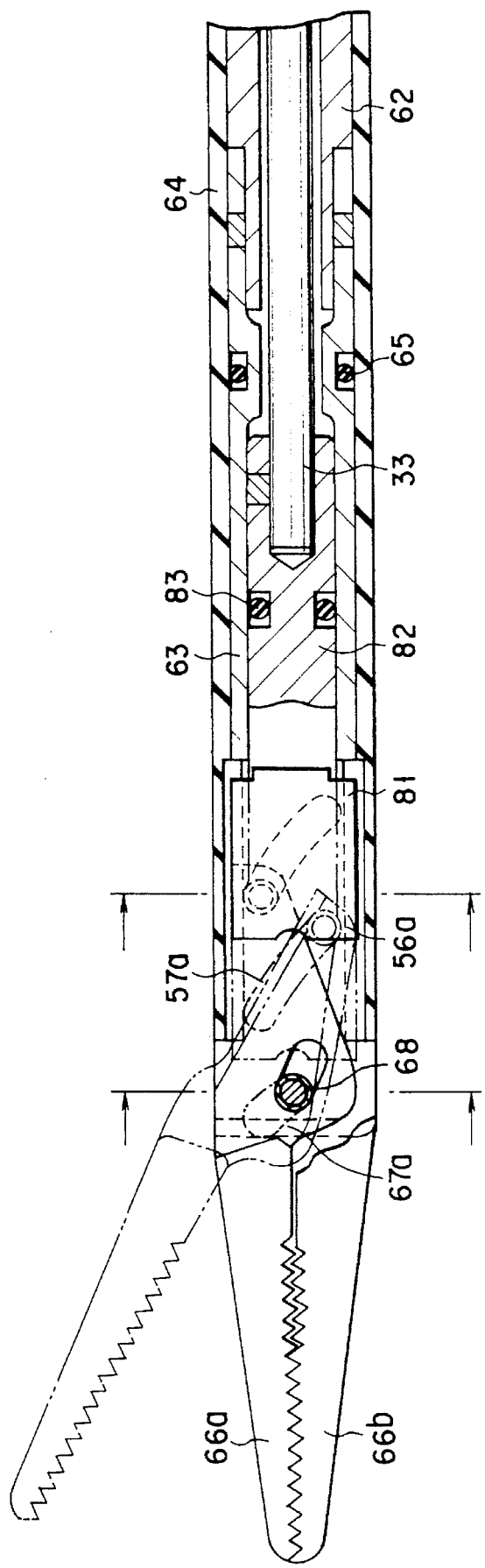
FIG. 26 is a sectional view of an insertion section of a forceps according to a seventh embodiment of the invention.

Both the forceps members 66a and 66b need not be rockable. As shown in FIG. 26 illustrating a seventh embodiment, for example, the forceps section may have a single-swing structure such that only the upper forceps member 66a can swing open.

Alternatively, the oval pin fitting holes 67a and 67b may be formed in the wall of the distal end portion of the insulating cover 63 so that the forceps members 66a and 66b and the support pin 68 can move together along the holes.

Figure 27:
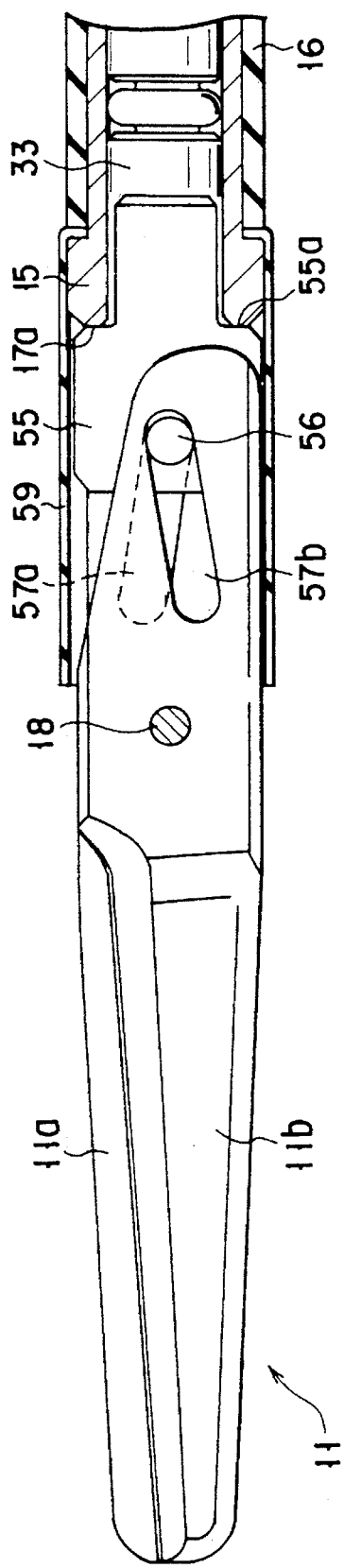
FIG. 27 is a sectional view showing a distal end portion of a forceps according to a modification of the first embodiment and its surroundings.
Figure 28:
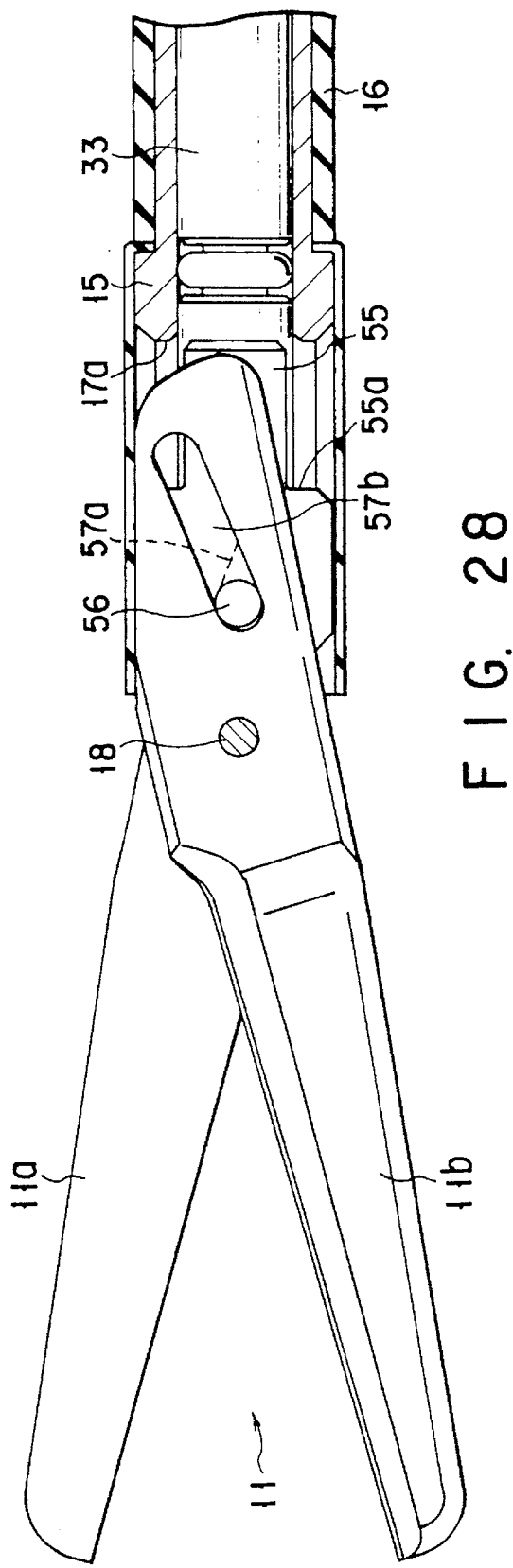
FIG. 28 is a sectional view showing the open-state distal end portion of the forceps according to the modification of the first embodiment and its surroundings.

FIGS. 27 and 28 show a modification of the forceps. As in the first embodiment, a pair of forceps members 11a and 11b are rockably supported on the distal end portion of a sheath 15 for use as a retaining member by means of a support pin 18. Straight cam grooves 57a and 57b, which are inclined with respect to the axial direction of a driving rod member 33, are formed in rear-end arm portions 21a and 21b of the forceps members 11a and 11b, respectively. The grooves 57a and 57b are inclined in opposite directions.

A connecting member 55 having a hole is attached to the distal end of the driving rod member 33, and a cam pin 56 is fitted in the hole of the member 55. The cam pin 56 is engagedly fitted in both the cam grooves 57a and 57b in the rear end portions of the forceps members 11a and 11b. The grooves 57a and 57b may be curved in the form of a circular arc, as shown in FIGS. 29 and 30, or extend along any desired curve.

As in the case of the first embodiment, therefore, the cam pin 56 is moved to the distal end side in the cam grooves 57a and 57b by advancing the driving rod member 33 by means of the operating section, so that the forceps members 11a and 11b rock relatively to each other around the support pin 18 to open, as shown in FIG. 28. The forceps members 11a and 11b are closed by reversely following the aforementioned procedure.

When the forceps members 11a and 11b are fully closed, the angle of contact between the support pin 18 and the cam grooves 57a and 57b is so narrow that a great force can be produced. If the pin 18 is broken, the pin 56 is caught by the end portions of the cam grooves 57a and 57b, so that the forceps members 11a and 11b can never fall off. When the members 11a and 11b are fully open, the contact angle is so wide that a short stroke can ensure a wide opening. The way of producing the force can be freely selected by changing the shape of the cam grooves 57a and 57b.

A stepped portion 55a at the rear end of the connecting member 55 and a rear end portion 17a of a distal slitted portion 17 of the sheath 15 abut against each other when the forceps section 11 is fully closed, and no force can be further applied to the operating mechanism side.

Figure 31:
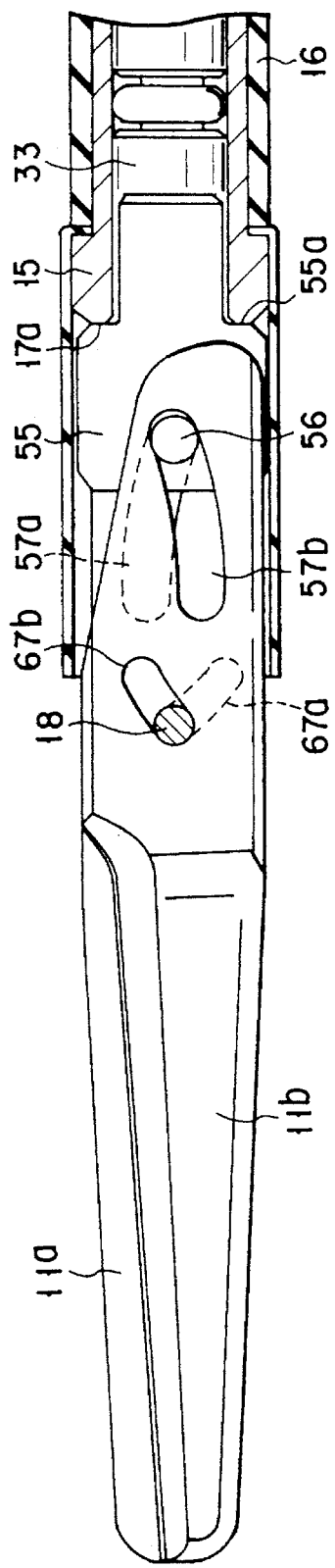
FIG. 31 is a sectional view showing a distal end portion of a forceps according to still another modification of the first embodiment and its surroundings.
Figure 32:
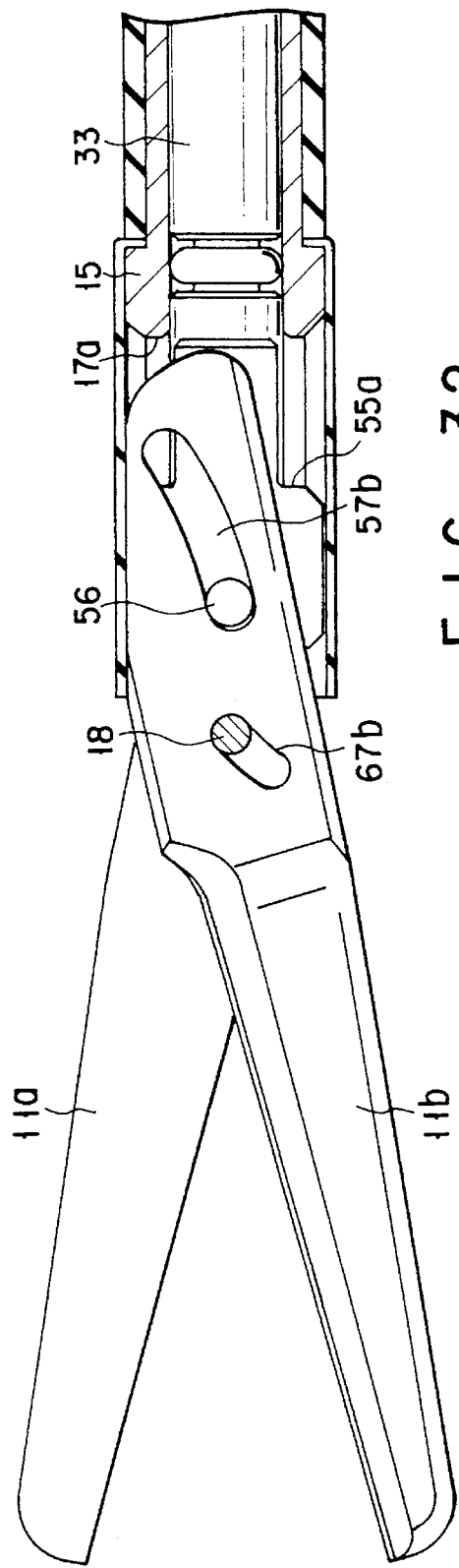
FIG. 32 is a sectional view showing the open-state distal end portion of the forceps according to the third modification of the first embodiment and its surroundings.

FIGS. 31 and 32 show an arrangement which incorporates the forceps member support system according to the fifth embodiment, in addition to the cam mechanism for open-close operation with the aforementioned construction. Slot-shaped pin fitting holes 67a and 67b are formed in the middle portions of the forceps members 11a and 11b, respectively, and a support pin 18 is passed through both these holes 67a and 67b.

Referring now to FIGS. 33A to 33D, an eighth embodiment of the present invention will be described. This embodiment is a modification of the forceps operating section. FIG. 33A shows an outline of a seizing forceps 100. Numeral 101 denotes the body of the seizing forceps. The proximal end portion of an insertion section 102 is connected to the forceps body 101 of this operating section, and an operating handle mechanism 103 is incorporated in the proximal end portion.

An openable seizing forceps section 105 is attached to the distal end portion of an elongate sheath 104 of the insertion section 102. The forceps section 105, which is constructed in the same manner as that of the foregoing seizing forceps, is connected to the distal end portion of an operating rod 109 which is disposed in the sheath 104 for movement in the axial direction. The seizing forceps section 105 is opened or closed as the operating rod 109 is moved by means of the operating handle mechanism 103.

The operating handle mechanism 103 includes a stationary handle 110 and a movable handle 111. Finger ring portions 110a and 111a are formed on the proximal end portions of the handles 110 and 111, respectively.

Formed on the distal end side of the stationary handle 110, moreover, are a movable handle junction 113, an insertion section fitting hole 110b in which the proximal end portion of the insertion section 102 is inserted, and a passage hole 110c for the operating rod 109. The proximal end portion of the sheath 104 of the insertion section 102 is inserted in and clamped to the fitting hole 110b by means of a fixing screw 112. The proximal end portion of the operating rod 109 in the sheath 104 extends through the passage hole 110c to the outside.

The distal end portion of the movable handle 111 is mounted on the movable handle junction 113 so as to be rockable around a rocking shaft 114. Arranged between the stationary handle 110 and the movable handle 111, moreover, are a seizing member drive mechanism section 115 for moving the operating rod 109 for operating the seizing forceps section 105 as the movable handle 111 is operated, and a retaining portion 116 for releasably retaining the handles 110 and 111 in a desired opening position.

The seizing member drive mechanism section 115 is provided with two link members 117 and 118. One end portion of the one link member 117 is connected so as to be rockable around a connecting pin 119 toward the movable handle 111. One end portion of the other link member 118 is connected so as to be rockable around a connecting pin 120 toward the stationary handle 110.

The respective other end portions of the link members 117 and 118 are rockably connected to the proximal end portion of a joint rod 122 by means of a connecting pin 121. The distal end portion of the rod 122 is connected to the proximal end portion of the operating rod 109 by means of a connecting member 123. As the movable handle 111 is moved, the two link members 117 and 118 of the seizing member drive mechanism section 115 swing. As the members 117 and 118 swing in this manner, the operating rod 109 is moved in the axial direction through the medium of the joint rod 122 and the connecting member 123, whereby the members of the seizing forceps section 105 are opened or closed.

FIG. 33D shows a junction at which the connecting member 123 is connected to the operating rod 109 and the joint rod 122. As shown in FIG. 33D, external and internal thread portions 123a and 123b are formed on the proximal and distal end portions of the connecting member 123, respectively. Further, an internal thread portion 122a to mate with the external thread portion 123a of the connecting member 123 is formed on the distal end portion of the joint rod 122, while an external thread portion 109a to mate with the internal thread portion 123b of the member 123 is formed on the proximal end portion of the operating rod 109.

Engagement pitches $P_1$ and $P_2$ between the joint rod 122 and the connecting member 123 and between the operating rod 109 and the member 123 are different ($P_1 \neq P_2$). The opening angle of the seizing forceps section 105 can be adjusted in a manner such that the overall length of the combination of the operating rod 109, connecting member 123, and joint rod 122 is changed by rotating the connecting member 123.

The retaining portion 116 is provided with a pair of engaging members 126 and 127. One end portion of the one engaging member 126 is fixedly screwed in the region near the finger ring portion 110a of the stationary handle 110, while one end portion of the other engaging member 127 is screwed in the region near the finger ring portion 111a of the movable handle 111. As shown in FIG. 33B, the engaging members 126 and 127 are formed having substantially serrated ratchets 126a and 127a, respectively. The ratchets 126a and 127a are opposed so as to be in mesh with each other. Each of the ratchets 126a and 127a may be provided with one or more serrate projections.

FIG. 33C shows a junction of the movable handle 111 at the movable handle junction 113 of the stationary handle 110. In this case, a fitting groove 110d for the movable handle 111 is formed in the junction 113. The width of the groove 110d is greater than the thickness of the movable handle 111.

when the movable handle 111 is fitted in the fitting groove 110d, gaps are formed between the handle 111 and opposite walls 128a and 128b of the groove 110d. These gaps allow the movable handle 111 to move in the direction to disengage the engaging members 126 and 127.

An external thread portion 114a is formed on one end portion of the rocking shaft 114 of the movable handle 111. The thread portion 114a is screwed in an internal thread portion 129 in the one wall 128a of the fitting groove 110d of the movable handle junction 113.

Moreover, a holding depression 130 for housing a head 114b of the rocking shaft 114 is formed in the other wall 128b of the fitting groove 110d, and the movable handle 111 is formed having a through hole 131 through which the shaft 114 is passed.

A support mechanism 132 for supporting the engaging members 126 and 127 for movement is arranged such that the movable handle 111 is moved along the rocking shaft 114 in the fitting groove 110d of the movable handle junction 113 of the stationary handle 110, whereby the members 126 and 127 are moved between a locked position where they are in engagement with each other and an unlocked position where they are disengaged.

The rocking shaft 114 is fitted with a Belleville spring (urging means) 133 in the gap between the movable handle 111 and the wall 128a of the fitting groove 110d of the movable handle junction 113. The spring 133 urges the engaging members 126 and 127 toward the locked position through the medium of the movable handle 111. The spring 133 has a thickness smaller than the gap width, so that it can be assembled with ease. A leaf spring, coil spring, or hydraulic mechanism may be used in place of the Belleville spring 133.

In assembling the seizing forceps body 101, the rocking shaft 114 is screwed in after the movable handle 111 and the Belleville spring 133 are fitted in the fitting groove 110d at the movable handle junction 113 of the stationary handle 110. Thereupon, the shaft 114 presses the movable handle 111, which presses the spring 133 in its turn. The spring 133 is compressed by the resulting force of pressure, and its repulsive force causes the movable handle 111 to push the engaging member 127 on its side so as to engage the engaging member 126 on the stationary-handle side. Thus, the engaging members 126 and 127 are urged toward the locked position where their respective ratchets 126a and 127a are in engagement with each other.

The following is a description of the function of the arrangement described above. Normally, the retaining portion 116, which releasably retains the stationary and movable handles 110 and 111 in the desired opening position, is urged by the urging force of the Belleville spring 133 at the movable handle junction 113 toward the locked position where the ratchets 126a and 127a of the engaging members 126 and 127 engage each other. Thus, there is no possibility of the ratchets 126a and 127a being disengaged from each other by mistake during use of the seizing forceps body 101.

In disengaging the ratchets 126a and 127a of the engaging members 126 and 127, it is necessary only to subject the movable handle 111 to a force in the direction opposite to the urging direction of the Belleville spring 133. In this case, the movable handle 111 moves along the rocking shaft 114 in the direction opposite to the urging direction of the spring 133, so that the engaging member 127 on the movable-handle side can be separated from the engaging member 126 on the stationary-handle side so that the ratchets 126a and 127a are disengaged from each other.

When the force applied to the movable handle 111 is reduced after the engaging members 126 and 127 are unlocked in this manner, the engaging members 126 and 127 can be restored to their initial state in which they are urged toward the locked position by the urging force of the Belleville spring 133.

In the arrangement described above, the support mechanism 132 for supporting the engaging members 126 and 127 for movement is designed so that the movable handle 111 is moved along the rocking shaft 114 in the fitting groove 110d of the movable handle junction 113 of the stationary handle 110, whereby the members 126 and 127 are moved between the locked position where they are in engagement with each other and the unlocked position where they are disengaged. Normally, moreover, the engaging members 126 and 127 are urged by the urging force of the Belleville spring 133 toward the locked position where their ratchets 126a and 127a engage each other. Accordingly, the components of the locking-unlocking mechanism of the retaining portion 116 can be reduced to simplify the structure, and the operating efficiency of the seizing forceps body 101 can be improved.

Since the engaging members 126 and 127 are urged by means of the urging force of the Belleville spring 133 toward the locked position where their ratchets 126a and 127a engage each other, moreover, the retaining portion 116 cannot be easily disengaged even when the handle mechanism 103 is operated involuntarily.

Further, the Belleville spring 133 is compressed by pressing the movable handle 111 with a force greater than the urging force of the spring 133, whereby the handle 111 can be moved correspondingly toward the unlocked position where the ratchets 126a and 127a of the engaging members 126 and 127 of the retaining portion 116 are disengaged. Thus, the retaining portion 116 can be engaged and disengaged even though the movable handle 111 cannot be bent to a particularly high degree.

FIG. 34 shows a ninth embodiment of the present invention. In this embodiment, the gaps are omitted which, according to the eighth embodiment, are provided at the movable handle junction 113 of the stationary handle 110 and allow the movable handle 111 to move in the direction to disengage the engaging members 126 and 127. According to the ninth embodiment, moreover, the stationary-handle-side engaging member 126 of the retaining portion 116 for releasably retaining the stationary and movable handles 110 and 111 in the desired opening position is mounted in a different way.

More specifically, according to this embodiment, a support portion for the engaging member 126 on the stationary-handle side is provided with a support mechanism 145 and a Belleville spring 146, as shown in FIG. 34. The mechanism 145 supports the engaging members 126 and 127 for movement between a locked position where the members 126 and 127 are in engagement with each other and an unlocked position where the members 126 and 127 are disengaged. The spring 146 urges the engaging members 126 and 127 toward the locked position.

In FIG. 34, numeral 141 denotes a mounting hole for the engaging member 126 on the side of the stationary handle 110. The hole 141 is greater than a mounting end portion 144 of the member 126 which is inserted therein.

When the mounting end portion 144 of the engaging member 126 is inserted in the mounting hole 141, gaps are formed between the portion 144 and opposite walls 142a and 142b of the hole 141. These gaps allow the movable handle 111 to move in the direction to disengage the engaging members 126 and 127.

Numeral 143 denotes a rocking pin which stretches between the opposite walls 142a and 142b of the mounting hole 141. The mounting end portion 144 of the engaging member 126 is supported on the rocking pin 143 for movement in the axial direction of the pin 143. The support mechanism 145 for supporting the engaging members 126 and 127 for movement is arranged so that the members 126 and 127 are moved between the locked position where they are in engagement with each other and the unlocked position where they are disengaged. Moreover, the rocking pin 143 is fitted with a Belleville spring 146 for urging the engaging members 126 and 127 toward the locked position.

Thus, in the arrangement described above, the support mechanism 145 for supporting the engaging members 126 and 127 for movement is arranged so that the mounting end portion 144 of the engaging member 126 is moved along the rocking pin 143, which stretches between the opposite walls 142a and 142b of the mounting hole 141, whereby the members 126 and 127 are moved between the locked position where they are in engagement with each other and the unlocked position where they are disengaged. Normally, moreover, the members 126 and 127 are urged by the urging force of the Belleville spring 146 toward the locked position where their ratchets 126a and 127a engage each other. Also in this case, the components of the locking-unlocking mechanism of the retaining portion 116 can be reduced to simplify the structure, and the operating efficiency of the seizing forceps body 101 can be improved, as in the eighth embodiment.

FIGS. 35A to 35C show a tenth embodiment of the present invention. FIG. 35A shows an outline of a seizing forceps. Numerals 151, 152 and 153 denote the body of the seizing forceps, an insertion section, and a handle mechanism for manual operation, respectively.

An openable seizing member, such as the one mentioned before, is attached to the distal end portion of an elongate sheath 154 of the insertion section 152. This movable-side seizing member is connected to the distal end portion of an operating rod 159, which is disposed in the sheath 154 for movement in the axial direction, by means of a cam mechanism.

The handle mechanism 153 is provided with a stationary handle 160 and a movable handle 161. Finger ring portions 160a and 161a are formed on the proximal end portions of the handles 160 and 161, respectively.

Formed on the distal end side of the stationary handle 160, moreover, are a movable handle junction 163, an insertion section fitting hole 160b in which the proximal end portion of the insertion section 152 is inserted, and a passage hole 160c for the operating rod 159. The proximal end portion of the sheath 154 of the insertion section 152 is inserted in and fixed to the fitting hole 160b by means of a fixing screw. The proximal end portion of the operating rod 159 in the sheath 154 extends through the passage hole 160c to the outside.

Formed in the distal end portion of the movable handle 161, furthermore, is an engaging groove 161b in engagement with a joint member 162 which is connected to the proximal end portion of the operating rod 159. The distal end portion of the movable handle 161 is mounted on the movable handle junction 163 so as to be rockable around a rocking shaft 170.

Arranged between the stationary handle 160 and the movable handle 161, moreover, is a retaining portion 164 which, constructed in the same manner as the retaining portion 116 of the eighth embodiment, releasably retains the handles 160 and 161 in a desired opening position.

The retaining portion 164 is provided with a pair of engaging members 165 and 166. One end portion of the one engaging member 165 is fixedly screwed in the region near the finger ring portion 160a of the stationary handle 160, while one end portion of the other engaging member 166 is screwed in the region near the finger ring portion 161a of the movable handle 161. As shown in FIG. 35C, the engaging members 165 and 166 are formed having substantially serrated ratchets 165a and 166a, respectively. The ratchets 165a and 166a are opposed so as to be in mesh with each other. Each of the ratchets 165a and 166a may be provided with one or more serrate projections.

FIG. 35B shows a junction of the movable handle 161 at the movable handle junction 163 of the stationary handle 160, which is constructed in the same manner as the one according to the eighth embodiment. More specifically, a fitting groove 169 for the movable handle 161 is formed in the junction 163. The width of the groove 169 is greater than the thickness of the movable handle 161.

When the movable handle 161 is fitted in the fitting groove 169, gaps are formed between the handle 161 and opposite walls 168a and 168b of the groove 169. These gaps allow the movable handle 161 to move in the direction to disengage the engaging members 165 and 166.

An external thread portion 170a is formed on one end portion of the rocking shaft 170 of the movable handle 161. The thread portion 170a is screwed in an internal thread portion 171 in the one wall 168b of the fitting groove 169 of the movable handle junction 163.

Moreover, a holding depression 172 for housing a head 170b of the rocking shaft 170 is formed in the other wall 168a of the fitting groove 169, and the movable handle 161 is formed having a through hole through which the shaft 170 is passed.

A support mechanism 173 for supporting the engaging members 165 and 166 for movement is arranged such that the movable handle 161 is moved along the rocking shaft 170 in the fitting groove 169 of the movable handle junction 163 of the stationary handle 160, whereby the members 165 and 166 are moved between a locked position where they are in engagement with each other and an unlocked position where they are disengaged.

The rocking shaft 170 is fitted with a Belleville spring 174 in the gap between the movable handle 161 and the wall 168a of the fitting groove 169 of the movable handle junction 163. The spring 174 urges the engaging members 165 and 166 toward the locked position through the medium of the movable handle 161.

Thus, in the arrangement described above, the support mechanism 173 for supporting the engaging members 165 and 166 for movement is arranged so that the movable handle 161 is moved along the rocking shaft 170 in the fitting groove 169 of the movable handle junction 163 of the stationary handle 160, whereby the members 165 and 166 are moved between the locked position where they are in engagement with each other and the unlocked position where they are disengaged. Normally, moreover, the members 165 and 166 are urged by the urging force of the Belleville spring 174 toward the locked position where their ratchets 165a and 166a engage each other. Accordingly, the components of the locking-unlocking mechanism of the retaining portion 164 can be reduced to simplify the structure, and the operating efficiency of the seizing forceps body 151 can be improved.

Figure 36:
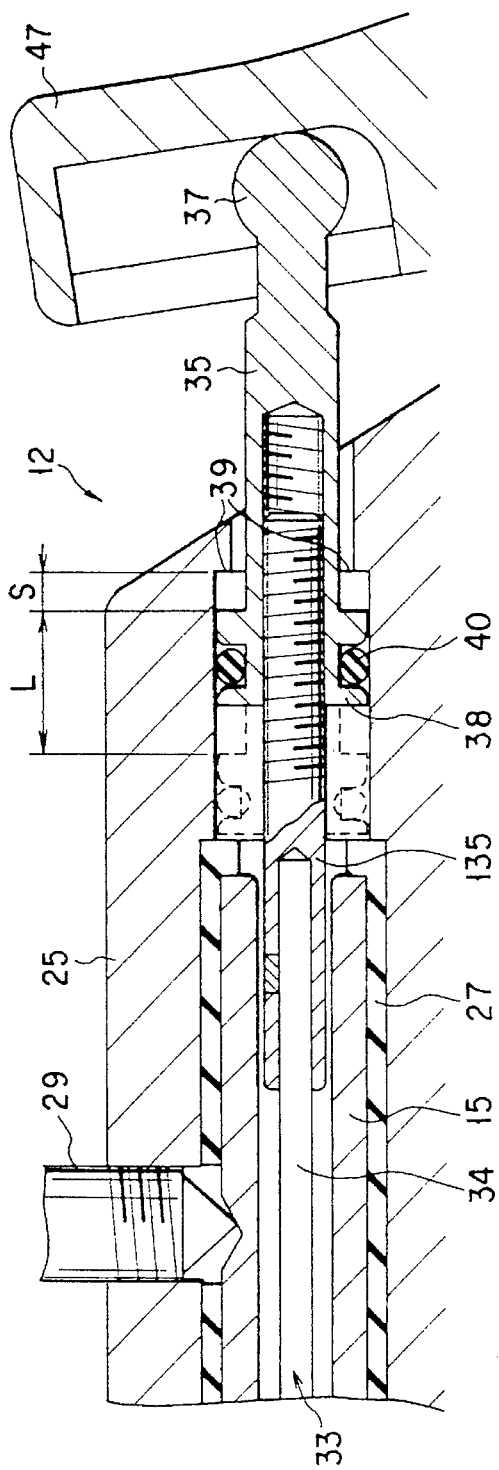
FIG. 36 is a sectional view showing the principal part of an operating section of a forceps according to a eleventh embodiment of the invention.

FIG. 36 shows a eleventh embodiment of the present invention. In this embodiment, at least one member of the driving rod member 33 according to the first embodiment, e.g., the rod body 34, is formed of an elastic material, such as stainless steel with a wide elastic region, superelastic alloy, etc. The rod body 34 and the rod member 33 are connected to each other by means of a connecting bar 135. When the rod member 33 is pulled, the forceps section is gradually closed. When an additional force is applied to the driving rod member 33 by means of the operating section after the forceps section is fully closed, the body 34 of the rod member 33 extends from its initial state. Thereupon, the rear end of the large-diameter portion 38 of the connecting rod 35 runs against the stepped portion 39, and the extension of the rod body 34 is s. Accordingly, any great force applied further to the operating section cannot be transmitted to the driving rod member 33.

If a force is applied by operating the movable operating handle 47 with the forceps section fully opened to seize an object, the driving rod member 33 extends by (L+s), the sum of its open-close stroke L and the extension s. This extension (L+s), which is the maximum extension of the rod member 33, is set within the elastic region of the rod body 34 of the rod member 33. In other words, there is a relation EL>(L+s), where L and EL is the stroke of the member 33 and the elastic-limit extension of the rod body 34, respectively. With this arrangement, the forceps section or its operating mechanism cannot be damaged even though the object is seized by the forceps section with an excessive force. Since the driving rod member 33 is operated with the extension within its elastic limit, moreover, it can be securely restored to its initial state.

If the sectional area and tensile strength of the rod body 34 are A mm$^2$ and $\sigma_\gamma$ kgf/mm$^2$, respectively, the rod body 34 is prevented from being subjected to a force higher than $\sigma_\gamma$ kgf/mm$^2$, by the agency of the stepped portion 39 as a stopper, even though a force of F kgf is applied such that there is a relation F/A>$\sigma_\gamma$. Since the extension (L+s) is set within the elastic region of the rod member 33, moreover, the rod body 34 is elastically restored to its initial length when the force on the operating section is removed. This system iS particularly suited to a seizing forceps.

FIGS. 37A to 37C show a twelfth embodiment of the present invention. A seizing forceps according to this embodiment is constructed substantially in the same manner as the ninth embodiment except that a pair of operating handles 263 and 264 are both movable, and that it is provided with a mechanism for restricting the extension of the operating rod member 109. Accordingly, the following is a description of only those particulars which differentiate the ninth embodiment from the thirteenth embodiment.

The first movable operating handle 263 is rockably connected to an operating section body 215 by means of a screw 273. Likewise, the second movable operating handle 264 is rockably connected to the body 215 by means of a screw 272. As shown in FIG. 38B, moreover, the screw 273 is provided with a Belleville spring 270 for urging the first handle 263, and the screw 272 with a Belleville spring 271 for urging the second handle 264.

The first movable operating handle 263 is connected to a connecting member 243 by means of a first link 266, while the second movable operating handle 264 is connected to the connecting member 243 by means of a second link 265. First and second ratchets 267 and 268 are fixed to the first and second handles 263 and 264, respectively. In this case, the ratchets 267 and 268 automatically engage each other when the operating handles 263 and 264 are closed.

When a force is applied to the handles 263 and 264 of the operating section, the operating rod member 109 is pulled toward the proximal side by means of the first and second links 266 and 265, so that the distance between the first and second ratchets 267 and 268 is shortened. The seizing forceps section is gradually closed as the rod member 109 is pulled. If an additional force is applied to the handles 263 and 264 of the operating section after the forceps section is fully closed, the rod member 109 extends from its initial state when a distal end 267b of the first ratchet 267 and a proximal end 268a of the second ratchet 268 (or a distal end 268b of the second ratchet 268 and a proximal end 267a of the first ratchet 267) run against each other, the distal forceps section cannot be further closed despite the greatest force on the operating section. If the extension of the operating rod member 109 at this time is a, any great force applied further to the operating section cannot be transmitted to distal end side of the rod member 109, so that the member 109 can be subjected only to a force which causes the member 109 to extend by a. If a force is applied to the handles of the operating section so that the distal end 267b and the proximal end 268a (or the distal end 268b and the proximal end 267a) run against each other with an object seized by means of the seizing section in its fully open state, the operating rod member 109 extends by (L+a). This extension (L+a), which is the maximum extension of the rod member 109, is also set within the elastic region of the member 109 according to this arrangement. In other words, the links 266 and 265 are arranged so that there is a relation EL>(L+a), where L and EL is the stroke and elastic-limit extension of the member 109, respectively.

Accordingly, this arrangement can provide the same function and effect as those of the foregoing embodiments. The extension a is the minimum necessary value for the operating rod member 109.

FIGS. 38A to 38C show a thirteenth embodiment of the present invention. A seizing forceps 280 of this embodiment is constructed in the same manner as the thirteenth embodiment except for the mechanism for restricting the extension of the operating rod member 109. In the restriction mechanism of this embodiment, the rear end of the connecting member 243 is caused to run against the respective side end edges of the ratchets 267 and 268.

Thus, when a force is applied to the operating handles of the operating section, the operating rod member 109 is pulled toward the proximal side by means of the first and second links 266 and 265, so that the distance between the first and second ratchets 267 and 268 is shortened. The seizing forceps section at the distal end is gradually closed as the rod member 109 is pulled. If an additional force is applied to the handles of the operating section after the forceps section is fully closed, the rod member 109 extends from its initial state. When the rear end of the connecting member 243 runs against the ratchets 267 and 268, the links 266 and 265 cease to operate, so that the forceps section cannot be further closed despite the greatest force on the operating section. If the extension of the operating rod member 109 at this time is b, any great force applied further to the operating section cannot be transmitted to distal end side of the rod member 109, so that the member 109 can be subjected only to a force which causes the member 109 to extend by b.

If a force is applied to the handles of the operating section so that the rear end of the connecting member 243 runs against the ratchets 267 and 268 with an object seized by means of the seizing section in its fully open state, the operating rod member 109 extends by (L+b). This extension (L+b), which is the maximum extension of the rod member 109, is set within the elastic region of the member 109. In other words, the length of the connecting member 243 is set so that there is a relation EL>(L+b), where L and EL is the stroke and elastic-limit extension of the member 109, respectively.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A surgical instrument for treatment in a body cavity, comprising:

an operating section including an operating handle;

a sheath for an insertion section, the sheath including a distal end portion to be inserted into the body cavity and a proximal end portion connected to the operating section;

at least one open-close member for treatment, the at least one open-close member being pivotally mounted on the distal end portion of the sheath by means of a pivot pin;

a cam mechanism connected to the at least one open-close member, the cam mechanism being situated nearer to the proximal end of the sheath than the position of the pivot pin, and the cam mechanism including an inclined cam and a cam pin in engagement with the cam, so that the at least one open-close member is rotated depending on the relationship between the cam pin and the cam, the component members of the cam mechanism having external shapes such that those portions on the proximal end side of the position near the pivot pin do not project from the sheath in every operating state;

a slot provided in the at least one open-close member and in which the pivot pin is fitted such that the slot is shiftable, the slot being inclined in the same direction as the inclined cam corresponding thereto; and a driving rod member passed through the sheath for reciprocation, and the driving rod member having a front end connected to the cam mechanism and a rear end connected to the operating section, the cam mechanism being activated to open and close the at least one open-close member for treatment as the driving rod member is moved by means of the operating handle of the operating section.

2. A surgical instrument according to claim 1, wherein:

said cam pin is attached to the proximal end portion of the at least one open-close member extending beyond the position of the pivot pin to the proximal end side; and said cam is formed in a member on the distal end of the driving rod member.

3. A surgical instrument according to claim 1, wherein the cam shape of said cam is inclined with respect to the moving direction of the driving rod member and extends along a curved line.

4. A surgical instrument according to claim 3, wherein curved line has a center of curvature which is situated ahead of the cam.

5. A surgical instrument according to claim 4, wherein said cam comprises a cam groove.

6. A surgical instrument according to claim 3, wherein said cam comprises a cam groove.

7. A surgical instrument according to claim 2, wherein said cam comprises a cam groove.

8. A surgical instrument according to claim 1, which further comprises:

an electrical connection port in the operating section for receiving an electrical jack member; and means for transmitting electric current from the electrical connection port to the at least one open-close member.

9. A surgical instrument according to claim 1, wherein said at least one open-close member includes a seizing mechanism during operation.

10. A surgical instrument according to claim 1, wherein said cam comprises a cam groove.

11. A surgical instrument according to claim 1, wherein: said cam is formed in the proximal end portion of the at least one open-close member extending beyond the position of the pivot pin to the proximal end side; and said cam pin is attached to a member on the distal end of the driving rod member.

12. A surgical instrument according to claim 11, wherein said cam comprises a cam groove.

13. A surgical instrument according to claim 1, which further comprises open-close means including a plurality of said open-close members for treatment, and wherein combinations of the cam pins and the cams corresponding to the respective open-close members are longitudinally deviated from one another with respect to the moving direction of the driving rod member.

14. A surgical instrument according to claim 1, wherein said at least one open-close member includes scissors blades during operative cutting.

15. A surgical instrument according to claim 1, wherein said driving rod member includes an elastic member adapted to extend from an initial state in accordance with a tensile force produced when the driving rod member is pulled by means of the operating handle of the operating section, and which further comprises stopper means for restricting the extension of the driving rod member within an elastic region of the elastic member.

16. A surgical instrument according to claim 1, which further comprises:

a pair of operating handles attached to the operating section;

a pair of engaging members releasably engaging each other in a desired opening position between the operating handles;

a sheath for an insertion section, the sheath including a distal end portion to be inserted into the body cavity and a proximal end portion connected to the operating section;

at least one open-close member for treatment, the at least one open-close member being pivotally mounted on the distal end portion of the sheath by means of a pivot pin;

a cam mechanism connected to the at least one open-close member, the cam mechanism being situated nearer to the proximal end of the sheath than the position of the pivot pin, and the cam mechanism including a cam and a cam pin in engagement with the cam, so that the at least one open-close member is rotated depending on the relationship between the cam pin and the cam;

a rod member passed through the sheath for reciprocation, and the rod member having a front end connected to the cam mechanism and a rear end connected to the operating section, the cam mechanism being activated to operate the at least one open-close member for treatment as the rod member is moved by means of the operating handle of the operating section;

operating means for retreating the cover means toward the proximal end of the sheath; and cover means covering the component members of the cam mechanism on the proximal end side of the region near the pivot pin, and the cover means having an outer peripheral surface substantially flush with the outer surface of the sheath.

17. A surgical instrument for treatment in the body cavity, comprising:

an operating section including an operating handle;

supporting means for holding the engaging members between a locked position where the engaging members are in engagement with each other and an unlocked position where the engaging members are disengaged; and means for urging the engaging members toward the locked position for engagement.

18. A surgical instrument according to claim 17, wherein said cover means includes an electrically insulating cylindrical member.

19. A surgical instrument according to claim 18, wherein said cam comprises a cam groove.

20. A surgical instrument according to claim 17, wherein said cam comprises a cam groove.

* * * * *